(12) United States Patent
Biernacki

(10) Patent No.: US 11,416,980 B2
(45) Date of Patent: Aug. 16, 2022

(54) WETWOOD DETECTION IN SAWN OR PLANED WOOD PRODUCTS

(71) Applicant: USNR, LLC, Woodland, WA (US)

(72) Inventor: Jacek M. Biernacki, Salmon Arm (CA)

(73) Assignee: USNR, LLC, Woodland, WA (US)

( * ) Notice: Subject to any disclaimer, the term of this patent is extended or adjusted under 35 U.S.C. 154(b) by 68 days.

(21) Appl. No.: 16/709,882

(22) Filed: Dec. 10, 2019

(65) Prior Publication Data

US 2020/0184620 A1    Jun. 11, 2020

Related U.S. Application Data

(60) Provisional application No. 62/777,260, filed on Dec. 10, 2018.

(51) Int. Cl.
| | |
|---|---|
| *G06T 7/00* | (2017.01) |
| *G06T 3/40* | (2006.01) |
| *G01N 21/898* | (2006.01) |

(52) U.S. Cl.
CPC ......... *G06T 7/001* (2013.01); *G01N 21/8986* (2013.01); *G06T 3/40* (2013.01); *G06T 2207/30161* (2013.01)

(58) Field of Classification Search
None
See application file for complete search history.

(56) References Cited

U.S. PATENT DOCUMENTS

| | | | | |
|---|---|---|---|---|
| 6,624,883 B1* | 9/2003 | Zhou | ...................... | G01B 11/30 250/559.25 |
| 8,581,142 B2* | 11/2013 | Colico | ...................... | B41M 5/24 219/121.68 |
| 8,662,121 B2* | 3/2014 | Stanish | ................... | B27B 1/007 144/356 |
| 2002/0080914 A1* | 6/2002 | West | ......................... | G01T 1/29 378/58 |
| 2002/0107644 A1* | 8/2002 | Meglen | .............. | G01N 21/3563 702/30 |
| 2002/0109093 A1* | 8/2002 | Kelley | .................. | G01N 21/31 250/339.09 |
| 2002/0113212 A1* | 8/2002 | Meglen | .............. | G01N 21/3563 250/339.05 |

(Continued)

FOREIGN PATENT DOCUMENTS

| | | |
|---|---|---|
| CN | 108254540 A | 7/2018 |
| EP | 1882935 A1 | 1/2008 |

OTHER PUBLICATIONS

Detection of knots in veneer surface by using laser scattering based on the tracheid effect. Tormanen et al. (Year: 2009).*

*Primary Examiner* — Delomia L Gilliard
(74) *Attorney, Agent, or Firm* — Schwabe, Williamson & Wyatt, P.C.

(57) ABSTRACT

The present disclosure provides embodiments of methods, systems, and apparatuses for detecting wet spots on machined surfaces of wood workpieces. Images of laser spots on a workpiece may be processed to determine area and aspect ratio values of the laser spots. Wet spots may be detected on the workpiece based at least on the area and aspect ratio values, and optionally based in part on color image data. A facility may use wet spot detection in grade determination and/or to classify wood pieces as 'wet' or 'dry' for the determination of appropriate drying conditions.

20 Claims, 13 Drawing Sheets

(56) References Cited

U.S. PATENT DOCUMENTS

| | | | |
|---|---|---|---|
| 2004/0206676 A1 | 10/2004 | Dai | |
| 2009/0208098 A1* | 8/2009 | Yang | G06T 1/60 |
| | | | 382/164 |
| 2014/0365463 A1* | 12/2014 | Tusk | G06F 16/51 |
| | | | 707/711 |
| 2017/0010356 A1* | 1/2017 | Demirel | G01B 11/25 |
| 2017/0023490 A1 | 1/2017 | Ahlen | |
| 2018/0313809 A1* | 11/2018 | Ursella | G01N 23/046 |

* cited by examiner

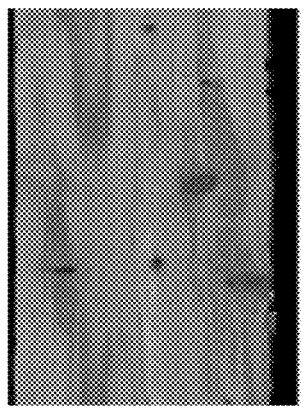   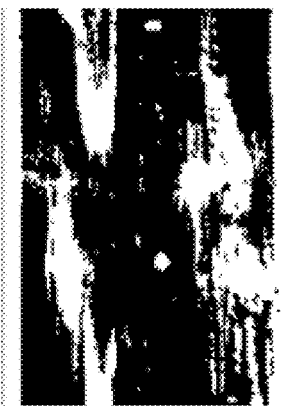
FIGURE 11A   FIGURE 11B   FIGURE 11C   FIGURE 11D
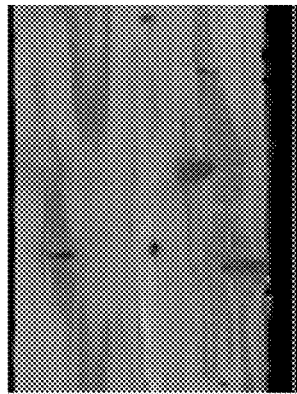  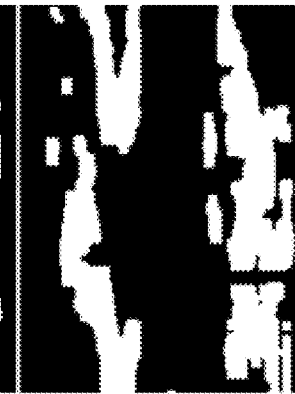 
FIGURE 12A   FIGURE 12B   FIGURE 12C   FIGURE 12D
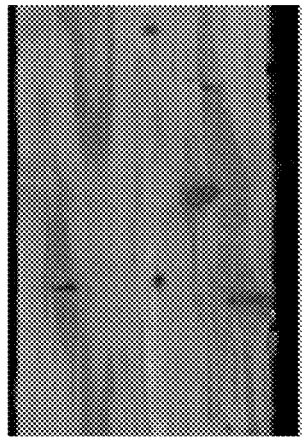 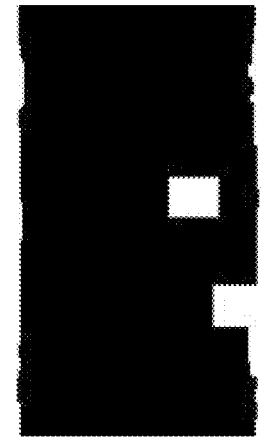 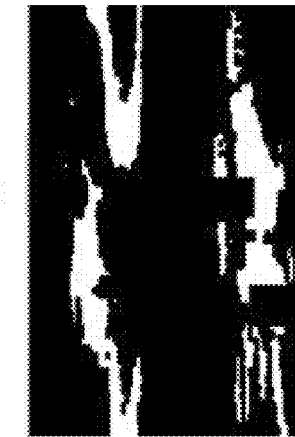 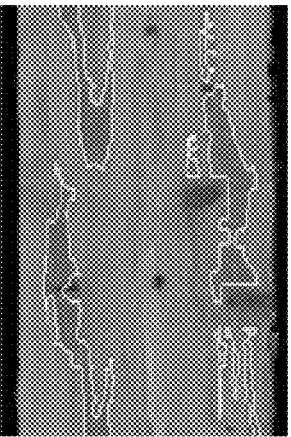
FIGURE 13A   FIGURE 13B   FIGURE 13C   FIGURE 13D

WETWOOD DETECTION IN SAWN OR PLANED WOOD PRODUCTS

CROSS REFERENCE TO RELATED APPLICATIONS

The present application claims priority to U.S. Provisional Patent Application No. 62/777,260, filed Dec. 10, 2018, entitled WETWOOD DETECTION IN SAWN OR PLANED WOOD PRODUCTS, the disclosure of which is hereby incorporated herein.

BACKGROUND

Large-scale lumber production facilities use kilns to dry batches of sawn boards to a desired moisture content. The undried 'green' lumber contains moisture in two forms—liquid water located within the cell lumens ('free water'), and water molecules bound within the cell walls ('bound water'). During the drying process, the free water typically is the first to be lost. When the free water has been lost, but the cell walls are still saturated with bound water, the wood is said to be at the fiber saturation point. The fiber saturation point is typically reached at a moisture content of about 25-30%. As the drying process continues and some of the bound water is lost, the moisture content of the wood drops below the fiber saturation point and the wood begins to shrink.

Because the outer surfaces of a board tend to reach the fiber saturation point before the interior of the board, drying boards too quickly can cause case hardening, cracking, checking, warping, and other drying defects. A slower drying process may help to avoid or reduce some drying defects, but it will reduce throughput and may increase overall energy use. The humidity, temperature, airflow, and other conditions within the kiln must be carefully controlled—typically according to a kiln schedule—to minimize drying defects and maximize throughput/efficiency. The kiln schedule is typically selected based on the wood species, thickness, and initial moisture content (and in some cases, other characteristics) of the lumber.

Even if all of the boards in a given batch have approximately the same average initial moisture content, one part of a board may be wetter than another part of the same board. Some boards may have localized regions of relatively high-moisture-content wood, commonly known as wetwood or wet spots. Sapwood tends to have a higher moisture content than heartwood, and in boards with both sapwood and heartwood, the moisture content of the sapwood areas may be higher than the heartwood areas. The distribution of moisture may also vary in accordance with the presence and location of pith and/or juvenile wood (corewood).

Boards with wet spots may require different drying schedules and drying conditions than boards with more uniform moisture distribution. Off-line methods are available to measure wood moisture content above the fiber saturation point. The oven-dry method is one example of an off-line method. Options for on-line moisture content detection above the fiber saturation point are unsatisfactory. On-line moisture meters, such as radiofrequency (RF) type meters, do not accurately detect moisture content in this range and offer very poor spatial resolution. Density-based scanners may be unable to distinguish between wetwood and higher-density defects such as knots.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIGS. 11A-D show a color image of a workpiece and corresponding thresholded color channel images of the workpiece;

FIGS. 12A-D show the color image of FIG. 11A and corresponding segmented aspect ratio, segmented area, and combined images, respectively of the workpiece;

FIGS. 13A-D show the color image of FIG. 11A and corresponding exclusions image, combined segmented image, and final color image with detected defect overlay, respectively, of the workpiece;

DETAILED DESCRIPTION OF DISCLOSED EMBODIMENTS

Figure 1:
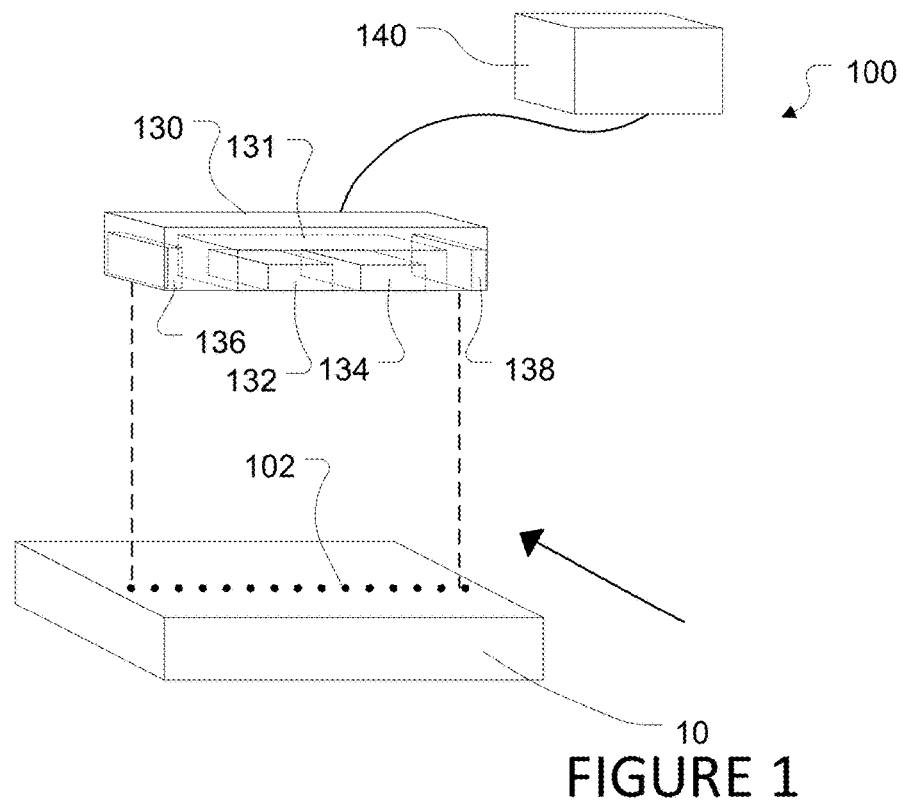
FIG. 1 is a schematic perspective view of a wet spot detection system.

In the following detailed description, reference is made to the accompanying drawings which form a part hereof, and in which are shown by way of illustration embodiments that may be practiced. It is to be understood that other embodiments may be utilized, and structural or logical changes may be made, without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, a computing device may be endowed with one or more components of the disclosed apparatuses and/or systems and may be employed to perform one or more methods as disclosed herein.

As used herein, the term "tracheid sensor" means a sensor that includes at least one laser light source operable to direct a beam of laser light onto a surface of a wood workpiece and at least one camera operable to capture an image of the resulting laser spot on that surface. For example, in some embodiments, a tracheid sensor may be a dot vector laser tracheid imaging sensor that includes a plurality of laser light sources configured to project a plurality of laser spots (e.g., a row of spots, or multiple rows, a cluster, or another pattern of spots) onto the surface of a wood workpiece and a line camera configured to capture images of the laser spots on that surface.

As used herein, the term "scanner" means an imaging device that includes at least one tracheid sensor. Thus, a scanner may be a tracheid sensor, or a combination of sensors that includes at least one tracheid sensor. Similarly, a scanner may include only one tracheid sensor or multiple tracheid sensors. In some embodiments, in addition to the tracheid sensor(s), a scanner may further include one or more additional sensors. For example, in some embodiments a scanner may include a color vision sensor, such as a high-definition (HD) color vision camera. For clarity, in the present disclosure, a scanner 'includes' all of the sensors that are arranged to capture data from any portion of the workpiece surface imaged by a tracheid sensor of that scanner. Thus, an additional sensor of a scanner may be located within the same housing as the tracheid sensor(s), or located within a separate housing.

As used herein, a "workpiece" is a piece of wood with at least one machined surface. Examples of workpieces include, but are not limited to, wood boards, cants, flitches, and slabs.

As used herein, the terms "heartwood" and "sapwood" have their conventional meanings. Generally, heartwood and sapwood are the inner and outer portions, respectively, of the xylem of a tree trunk. In a living tree, the xylem tissues of heartwood are generally dead/inactive and the sapwood xylem tissues are generally live/active.

As used herein, "wetwood" is wood that contains liquid water within the cell lumens or has a moisture content that exceeds the fiber saturation point (FSP) of the wood. As used herein, a "wet pocket" is a region of heartwood that contains liquid water within the wood cell lumens or has a moisture content that exceeds the fiber saturation point (FSP) of the heartwood. Similarly, the term "wet spot" refers to the portion (if any) of a wet pocket that is exposed on a machined surface of a workpiece. For clarity, wet pockets are three-dimensional regions and wet spots are two-dimensional areas, but both terms are used exclusively in reference to heartwood. As an example, if a heartwood cant with an interior wet pocket is cut lengthwise into two pieces along a cutting plane that extends through the interior wet pocket, each of the resulting pieces will include a corresponding portion of the wet pocket and a corresponding wet spot on the respective surface.

The present disclosure provides embodiments of methods, systems, and apparatuses for detecting wet spots on machined surfaces of wood workpieces, such as boards, flitches, cants, or the like. Such embodiments may enable rapid, specific, and non-destructive detection of wet spots at speeds adequate for use in modern sawmills, planer mills, and other wood processing facilities. A facility may use wet spot detection in grade determination and/or to classify wood pieces as 'wet' or 'dry' for the determination of appropriate drying conditions.

When laser light is projected onto a cut surface of a wood workpiece, such as a board or a flitch, some of the light scatters within the wood to form a 'scatter ellipse.' The light "wicks" along the lumens of the cells and becomes elongated in the direction of the fiber, along the axis of the grain. As the fiber in normal wood is generally unidirectional, a generally cylindrical laser beam projected onto a surface of normal wood (e.g., along a face or side of a board) forms an elliptical spot with its major axis oriented in the direction of the wood fiber.

Wood grain diverges around knots. This divergence causes round laser spots projected onto opposite sides of the knot to elongate in different directions relative to the longitudinal axis of the board. A round laser spot projected onto a knot forms a spot with a more circular shape than round laser spots projected onto normal wood. Thus, the shape and direction of laser spots on the surface of a board can be used to map a board's grain structure and the location and size of knots, and to correctly identify anomalies such as grease marks and other visible non-defects that may otherwise be misidentified by color vision-based imaging alone.

Knots and wet spots tend to be darker in color than normal wood. Moreover, a round laser spot projected onto a wet spot also retains a relatively circular shape, because free water in the lumens of the cells at the surface of the workpiece attenuates the wicking of the laser light along the fiber. However, the free water also causes spreading of the laser spot on the surface of the wood. As a result, laser spots projected onto wet spots tend to be larger than laser spot projected onto knots.

Therefore, in accordance with various embodiments, a wet spot on a surface (e.g., a face or a longitudinal side) of a workpiece may be identified based at least in part on the aspect ratio and area of laser spots on that surface. In various embodiments, a wet spot detection method may include obtaining an image of a laser spot on a surface of a wood workpiece, determining the aspect ratio and the area of the laser spot based on the image, comparing the determined aspect ratio to an aspect ratio threshold value, comparing the determined area to an area threshold value, and identifying a corresponding portion of the surface as a wet spot area based at least in part on a determination that the aspect ratio is less than the aspect ratio threshold value and that the area exceeds the area threshold value.

Optionally, the angle of the laser spot on the workpiece surface may also be used to identify or confirm the identification of a wet spot. While laser spots on normal wood tend to show at least some directionality, with the major axes of the spots generally parallel to the longitudinal axis of the workpiece, the angles of laser spots on wet spots may be more random. Therefore, in some embodiments a wet spot detection method may also include determining the angle of the laser spot based on the image and determining that the angle is not within a range of expected angles (e.g., of laser spots on clear dry wood). However, in other embodiments wet spots may be detected without the use of laser spot angle data.

In some embodiments, laser spot image data may be used in combination with data from another type of sensor to detect wet spots. For example, a combination of tracheid sensor image data and color image data may be used to detect wet spots. Thus, in some embodiments the method may further include obtaining a color image of the corresponding portion of the surface, determining a color of the corresponding portion of the surface based on the color image, comparing the color to a color threshold value, and identifying the corresponding portion of the surface as a wet spot based at least in part on a determination that the color of the corresponding portion of the surface is darker than the color threshold value. In other embodiments, wet spots may be detected without the use of color image data.

In various embodiments, a wet spot detection system may include a scanner and a computer system operatively coupled with the scanner. Some embodiments of the wet spot detection system may include only one scanner. Other embodiments of the wet spot detection system may include two or more scanners. Similarly, a scanner may include only one tracheid sensor or multiple tracheid sensors. Optionally, in some embodiments a scanner may further include at least one additional sensor. For example, in some embodiments a scanner may include a color vision camera, such as a high-definition (HD) color vision camera. Again, any additional sensor that detects or images the same part of the workpiece surface as a tracheid sensor of a scanner is considered part of that scanner, regardless of whether the additional sensor and tracheid sensor are located within the same housing.

In various embodiments, a scanner may be positioned above, below, or to one side of a path of workpiece flow. The scanner(s) and respective sensor(s) may be arranged for transverse scanning or lineal scanning. In a transverse scanning configuration, the scanner(s) or sensor(s) thereof may be arranged across the path of flow to scan workpieces that are oriented transverse to the path of flow (i.e., with the long axis of the workpiece generally perpendicular to direction of workpiece travel). Examples of scanners suitable for use in transverse-scanning embodiments include, but are not limited to, Bioluma LVG™ and Bioluma LVG+™ (trademarks of USNR). In other embodiments, the scanner(s) or sensor(s) thereof may be arranged to scan workpieces as they are moved in a lineal orientation (i.e., with the longitudinal axis of the workpieces oriented generally parallel to the direction of flow).

In embodiments with multiple scanners, groups of scanners may be arranged such that the fields of view of adjacent scanners overlap to some extent. Likewise, multiple scanners may be arranged to form a single scan zone, and/or arranged at intervals along the direction of flow to enable more rapid scanning. Regardless, the scanners may be positioned above and below, on opposite sides of, and/or around the path of flow.

A scanner may be positioned in-axis or off-axis. A scanner positioned 'in-axis' is positioned to view the workpiece along a line of sight that is substantially normal to the plane of a face, a longitudinal side, or an end of the workpiece, such that the scanner acquires data from one surface of the workpiece. A scanner positioned 'off-axis' is positioned to view the workpiece at an oblique angle (i.e., at an angle not perpendicular or parallel to a face, longitudinal side, or end), such that the scanner acquires data from a two surfaces (e.g., a face and a longitudinal side, or a face and an end, or a longitudinal side and an end) of the workpiece, thereby allowing the scanner to image at least part of both surfaces. In some embodiments with multiple scanners, all of the scanners may be positioned in-axis, or all of the scanners may be positioned off-axis, or at least one of the scanners may be positioned in-axis and another of the scanners may be positioned off-axis. In some scanners that include a color vision camera, the color vision camera may be positioned in-axis and the tracheid sensor may be positioned off-axis, or vice versa.

In various embodiments, a tracheid sensor of a scanner may acquire an image of laser spots on a portion of a surface (e.g., a face or a side) of a wood workpiece as the workpiece moves along the path of flow through the field of view of the scanner. If the scanner includes a color vision sensor, the color vision sensor may also acquire a color vision image of the same portion of that surface. The computer system may receive the image data from the scanner. The computer system may use the tracheid sensor image data to determine an aspect ratio value and an area value for some or all of the laser spots. The computer system may analyze the determined aspect ratio and area values to determine whether any of the laser spots has a relatively low aspect ratio and a relatively large area. In response to identifying such a laser spot, the computer system may determine that the corresponding area of the workpiece surface has a wet spot. If the image data includes color vision image data, the computer system may process the color vision image data to identify relatively dark areas of the workpiece surface. In response to identifying a laser spot with a relatively low aspect ratio and a relatively large area, and determining that the corresponding area of the workpiece surface is relatively dark, the computer system may determine that the area has a wet spot.

More specifically, in some embodiments the computer system may process the received tracheid sensor image data by using a correction algorithm to equalize the outputs of the camera sensor units (e.g., pixels) and/or to correct image distortions. Optionally, the computer system may also use a monitoring algorithm to identify potentially inaccurate image data resulting from sensor lens contamination. In that case, in response to identifying the potentially inaccurate image data, the computer system may send an alarm to an operator to notify the operator of the contamination, and/or may flag the potentially inaccurate image data as unusable tracheid sensor image data. Regardless, the computer system may use the processed tracheid sensor image data to determine the laser spot aspect ratio and area values. The computer system may convert the determined aspect ratio and area values to corresponding pixel values to generate an aspect ratio image and an area value image, respectively, of the surface portion of the workpiece. If the computer system receives color vision image data, the computer system may process the color vision image data to generate three color images (a red, a green, and a blue image) of the surface portion of the workpiece.

The computer system may segment each of the generated images based on pixel value and combine the segmented images (e.g., with an AND operation) to differentiate between regions of potential interest—e.g., regions that were relatively dark in the color images and in which the laser spots were relatively round and relatively large—and other regions of the image. The computer system may process the combined image to exclude defects and workpiece edges, and/or perform dilation/erosion operations. The computer system may segment the resulting image to define any wet spots. Optionally, the computer system may perform a similar process to define wet spots along at least one additional surface of the workpiece (e.g., the opposite face of the board, or another portion of the same face), and combine all of the wet spot information for the workpiece. The computer system may sum the detected wet spots and compare the resulting value to a predetermined value to determine whether to classify the workpiece as 'wet' material or 'dry' material. In some embodiments, the computer system may assign the workpiece to a drying schedule based at least on the classification. Optionally, the computer system may send an instruction to a machine center to thereby divert the wood workpiece from the path of flow and/or to designate the workpiece as wet material (e.g., by printing or projecting a label onto the workpiece). Although the description below describes the detection of wet spots, the systems and methods described herein may also be used to detect sapwood.

FIG. 1 illustrates an example of a wet spot detection system 100, in accordance with various embodiments. Wet spot detection system 100 includes at least one scanner 130 and a computer system 140 operatively coupled with the scanner 130. Scanner 130 may be positioned to scan a surface (e.g., a face and/or a longitudinal side) of a wood workpiece, such as a board, flitch, or cant. Computer system 140 may be configured to receive and process data from scanner 130. In particular, computer system 140 may be programmed with instructions operable, upon execution by a processor, to perform some or all of the operations of a wet pocket detection method as described herein.

Scanner 130 may be, or may include, a tracheid sensor 131. Tracheid sensor 131 may include a camera 132 and a laser light source 134. While FIG. 1 shows a tracheid sensor with only one laser light source and only one camera, in other embodiments the tracheid sensor may include multiple laser light sources and/or multiple cameras. The laser light source(s) 134 and camera(s) 132 may be arranged together in a single housing, or in separate housings, in any suitable manner.

Laser light source 134 may be any type of light source configured to emit a beam of laser light. For example, in some embodiments laser light source 134 may be a laser diode. Preferably, laser light source 134 is operable to direct a laser spot, or a pattern (e.g., a line) of laser spots, onto the surface of the workpiece.

Camera 132 may be any type of camera suitable for use to capture an image of the projected laser light on the surface of the workpiece. For example, camera 132 may be a line camera or an area camera.

In some embodiments, tracheid sensor 131 may be a dot vector laser tracheid imaging sensor with a plurality of laser light sources 134 arranged to project a row of laser spots along the workpiece surface and respective cameras 132 (e.g., line cameras) arranged to capture images of the laser spots on that surface. Optionally, tracheid sensor 131 may be a commercially available tracheid sensor known for use in wood processing facilities (e.g., sawmills, planer mills, veneer/plywood mills, etc.) to detect wood fiber orientation. Likewise, in some embodiments scanner 130 may be a conventional or commercially available scanner that includes at least one tracheid sensor.

Optionally, system 100 may further include one or more additional types of sensors and/or light sources. Other possible sensor types include, but are not limited to, color vision sensors, geometric sensors (e.g., a laser profile sensor, a structured light imaging sensor, a time-of-flight sensor, a stereo imaging sensor), an X-ray sensor, an ultrasound sensor, a vibration sensor, a radiofrequency (RF) sensor, and/or any other type of sensor that is operable to detect a position, location, or physical characteristic of a wood workpiece. Other possible light sources include, but are not limited to, other laser light sources, LED lights, incandescent lights, and any other light sources suitable for use to illuminate the workpiece or some portion thereof. If present, an additional sensor and/or light source may be located within the same housing as tracheid sensor 131 or provided in a separate housing and/or as a component of another scanner.

For example, in some embodiments scanner 130 may include a color vision sensor 136 and/or a laser profile sensor 138. Color vision sensor 136 may be a color vision camera suitable for use to collect color images of wood workpieces. Laser profile sensor 138 may be any laser profile sensor suitable for use to collect geometric profiles of wood workpieces. Optionally, color vision sensor 136 and laser profile sensor 138 may be conventional and/or commercially available sensors known for use to scan lumber, logs, or other wood workpieces. In particular embodiment, scanner 130 may include an elongate and generally rectangular housing, and a pair of color vision sensors 136, a pair of laser profile sensors 138, and a pair of tracheid sensors 131 (each with a respective camera 132 and two laser light sources 134) substantially enclosed within the housing. In other embodiments scanner 130 may have one or more additional sensors in addition to, or instead of, color vision sensor 136 and/or laser profile sensor 138. Still other embodiments of the wet spot detection system may lack sensors and/or light sources other than tracheid sensor(s) 131.

In some embodiments, scanner 130 may be configured to scan workpieces that are oriented generally transverse to the direction of flow. In other embodiments, scanner 130 may instead be configured to scan workpieces that are oriented generally parallel to the direction of flow (i.e., with the long axes of the workpieces generally parallel to the direction of workpiece travel). In either case, scanner 130 may be positioned either in-axis or off-axis.

While FIG. 1 illustrates an example of a system with only one scanner 130, other embodiments of the wet spot detection system include multiple scanners 130. The scanners 130 may be arranged above, below, to one or both sides of, and/or around the path of flow in any suitable manner to scan some or all of the surfaces of workpieces moving through the field(s) of view of the scanners. Scanners 130 may be arranged to form a single scan zone along the flow path or arranged at intervals in the flow direction (either singly or in groups) to form multiple scan zones. One of the scanners 130 may be positioned in-axis and another may be positioned off-axis, or all may be positioned in-axis, or all may be positioned off-axis. Similarly, if the scanners have multiple sensors/cameras, one sensor/camera of a scanner may be positioned in-axis and another sensor/camera of the scanner may be positioned off-axis; alternatively, all of the sensors may be positioned in-axis or all may be positioned off-axis.

Referring still to FIG. 1, system 100 may operate generally as follows. A workpiece 10 may be moved along the flow path (e.g., on a conveyor or by opposed feed rolls) in a direction of travel (arrow). As the workpiece enters the scan zone (in this example, the field of view of camera 132), the laser light source 134 may emit one or more beams of laser light onto the workpiece 10. For example, the laser light source 134 may project a row of generally round laser beams onto a surface of the workpiece. The camera 132 may capture images of the resulting laser spot(s) 102 on the workpiece surface. This process may be repeated any number of times as the workpiece passes through the scan zone, such that the camera 132 captures images of laser spots on respective surface portions of the workpiece at increments along the length and/or across the width of the workpiece. (If present, color vision sensor 136 may capture images of the surface.) Optionally, scanner 130 or the respective sensor(s) may process the captured images, such as by filtering the raw data, assembling the raw or filtered data into an image of the workpiece or portion thereof, and/or applying other image processing techniques.

Scanner 130 or the respective sensor(s) may send the image data to computer system 140. The image data may be sent in any suitable manner and format. For example, scanner 130 may be configured to send pixel values as they are generated, or to accumulate them into successive frames and send the frames as they are generated, or to accumulate all of the frames for a given workpiece into an image before sending the image to the computer system 140.

Figure 2A:
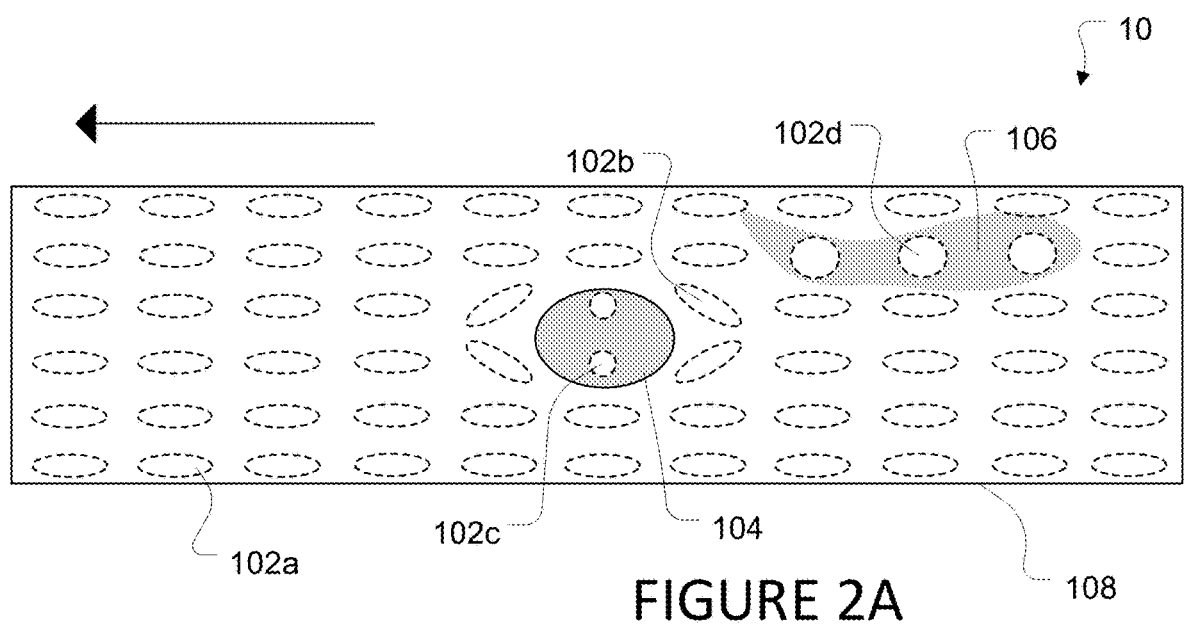
FIG. 2A is a schematic diagram of an image of laser spots on a surface of a workpiece.
Figure 2B:
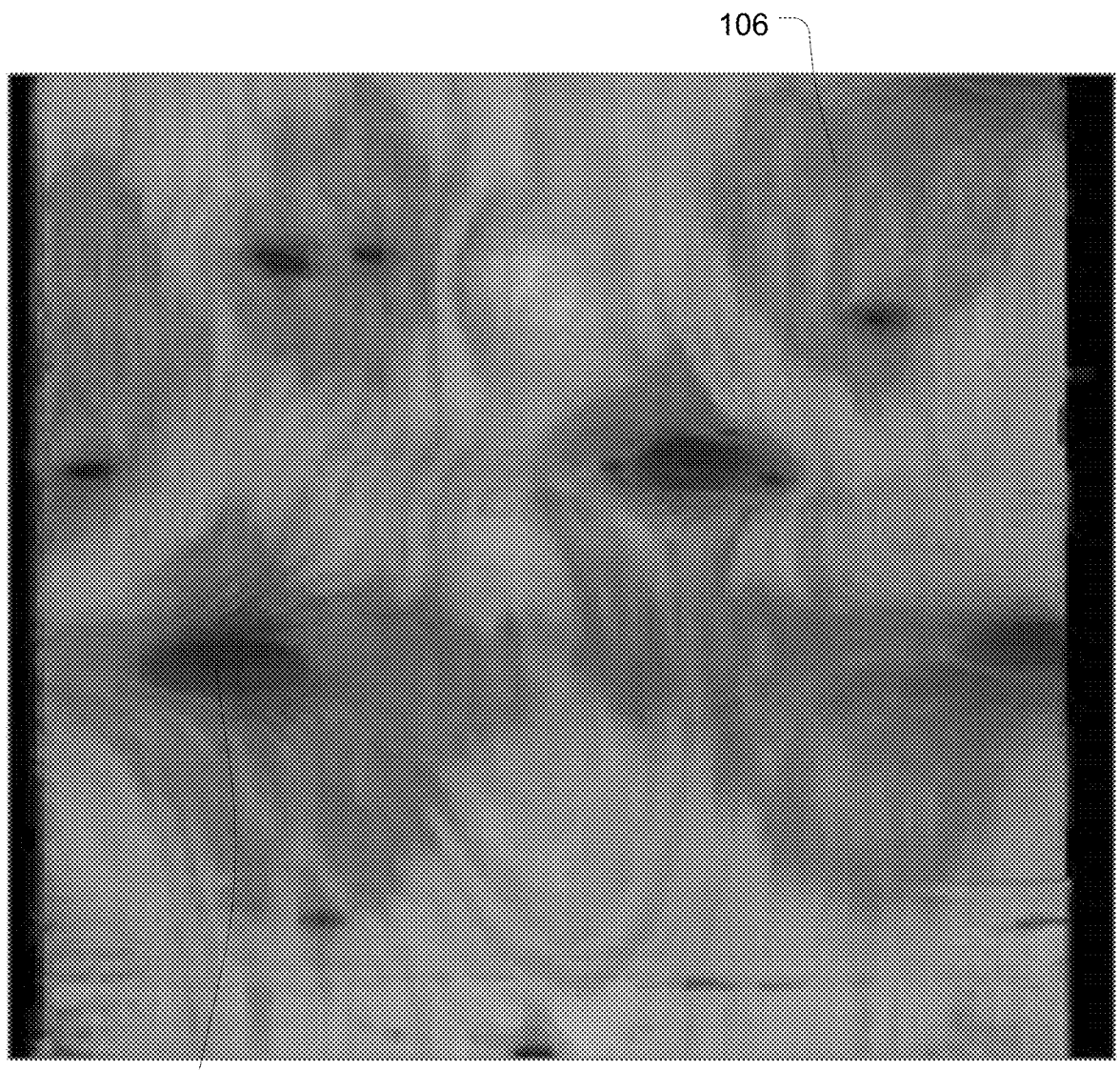
FIG. 2B is an image of a workpiece with knots and wet spots.
Figure 3A:
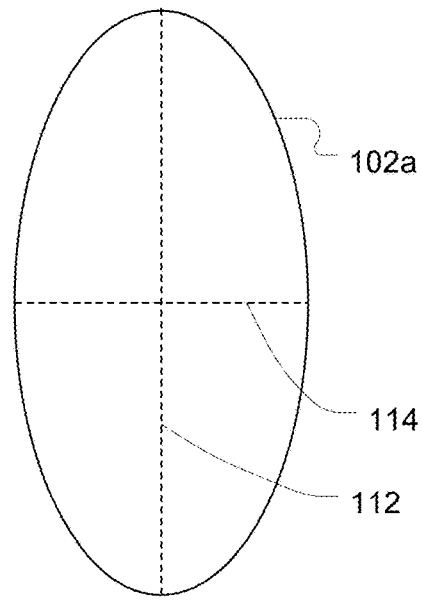
FIGS. 3A-D are schematic diagrams of laser spot images.
Figure 3B:
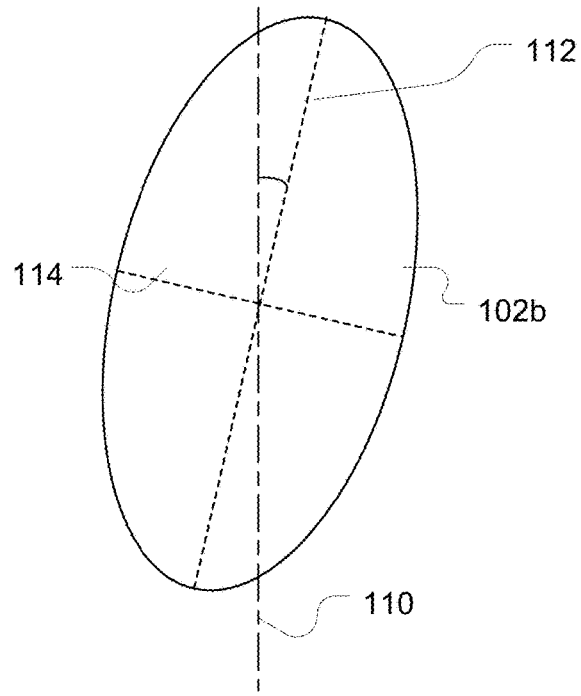
Figure 3C:
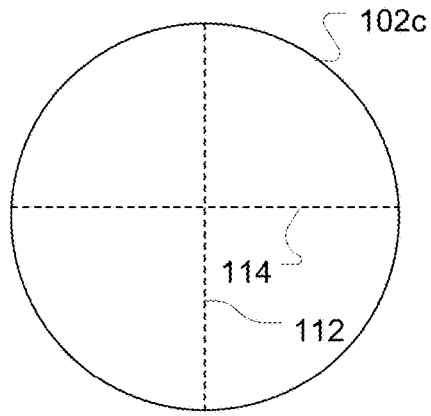
Figure 3D:
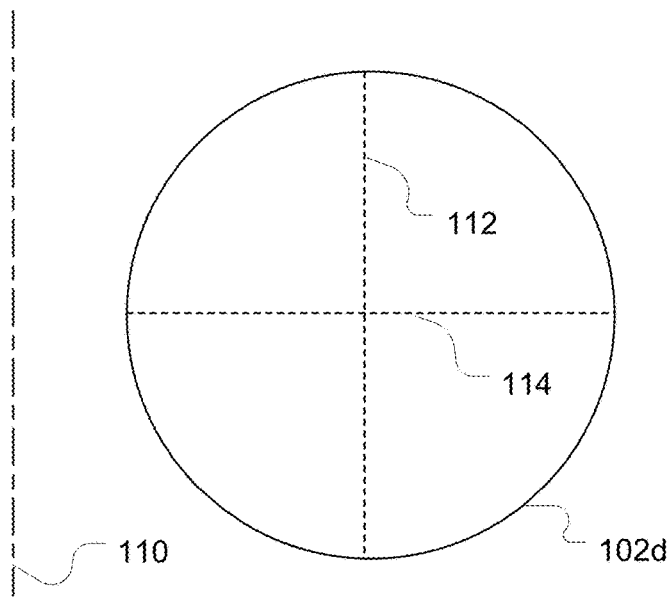

FIG. 2A is a schematic diagram of an image 108 of laser spots on a surface of a workpiece 10, in accordance with various embodiments. In this example, laser spot 102a is on a portion of 'clear' wood (i.e., straight-grained and without defects), and is therefore elongated in the direction of the wood grain (arrow), which is generally parallel to the longitudinal axis of the workpiece. Laser spot 102b, which is located near the outer edge of a knot 104, is elongated in a direction that is transverse to the longitudinal axis. Laser spot 102c is on knot 104, and laser spot 102d is on a wet spot 106. Laser spots 102c and 102d are less elongated (more circular) than laser spots 102a and 102b, and laser spot 102d is larger in diameter than laser spot 102c. An image of a workpiece with knots 104 and wet spots 106 is shown in FIG. 2B.

For clarity, a laser spot is considered to have a "major axis," which is the longest diameter of the laser spot; a "center," which is a point that lies along the major axis equidistant between the opposite ends of the major axis; and a "minor axis," which extends through the center of the laser spot and perpendicular to the major axis. FIGS. 3A-D are schematic diagrams of laser spots as shown in FIG. 2A, each with a major axis 112, a minor axis 114, and a center located at the intersection thereof. The length of each laser spot is its length along the major axis 112, and the width of the laser spot is its width along the minor axis 114. In some embodiments, the aspect ratio of a laser spot may be determined as the ratio of the length to the width. In that case, an elliptical laser spot with a length that is twice its width would have an aspect ratio of 2:1, or 2.0. Alternatively, the aspect ratio could instead be determined as the ratio of the width to the length, in which case an elliptical laser spot with a length that is twice its width would have an aspect ratio of 1:2, or 0.5. In either case, a laser spot that is perfectly round would have an aspect ratio of 1:1, or 1.0.

Computer system 140 may analyze the received laser spot image data to determine an area value and an aspect ratio value for a laser spot on a surface portion of the workpiece. If scanner 130 includes color vision sensor 136, the computer system may also use the received color image data to determine a color value for the surface portion. In some embodiments the computer system may process the laser spot image data and/or the color image data before determining the respective values, such as by using various filtering, thresholding, scaling, and/or other image processing techniques to compress or simplify the data, eliminate inaccurate data, and/or compensate for missing or eliminated data. Regardless, once the computer system has determined the area and aspect ratio values (and optionally, the color value), the computer system may compare the determined values to respective threshold values and determine, based on the comparison, whether a wet spot is present at that location on the workpiece.

Figure 4A:
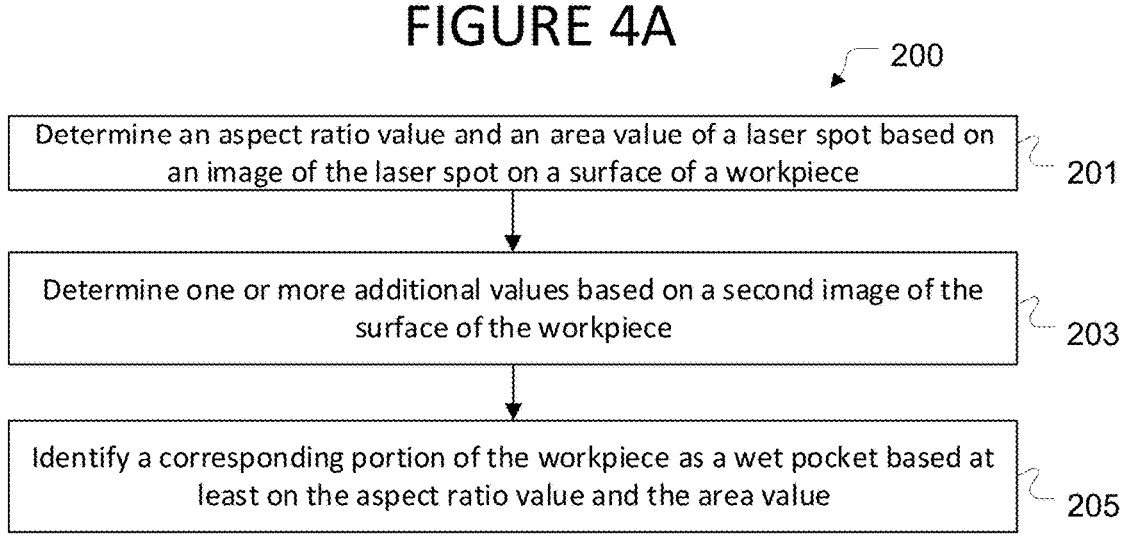
FIG. 4A is a flow diagram of a method of identifying wet spots along a wood workpiece.
Figure 4B:
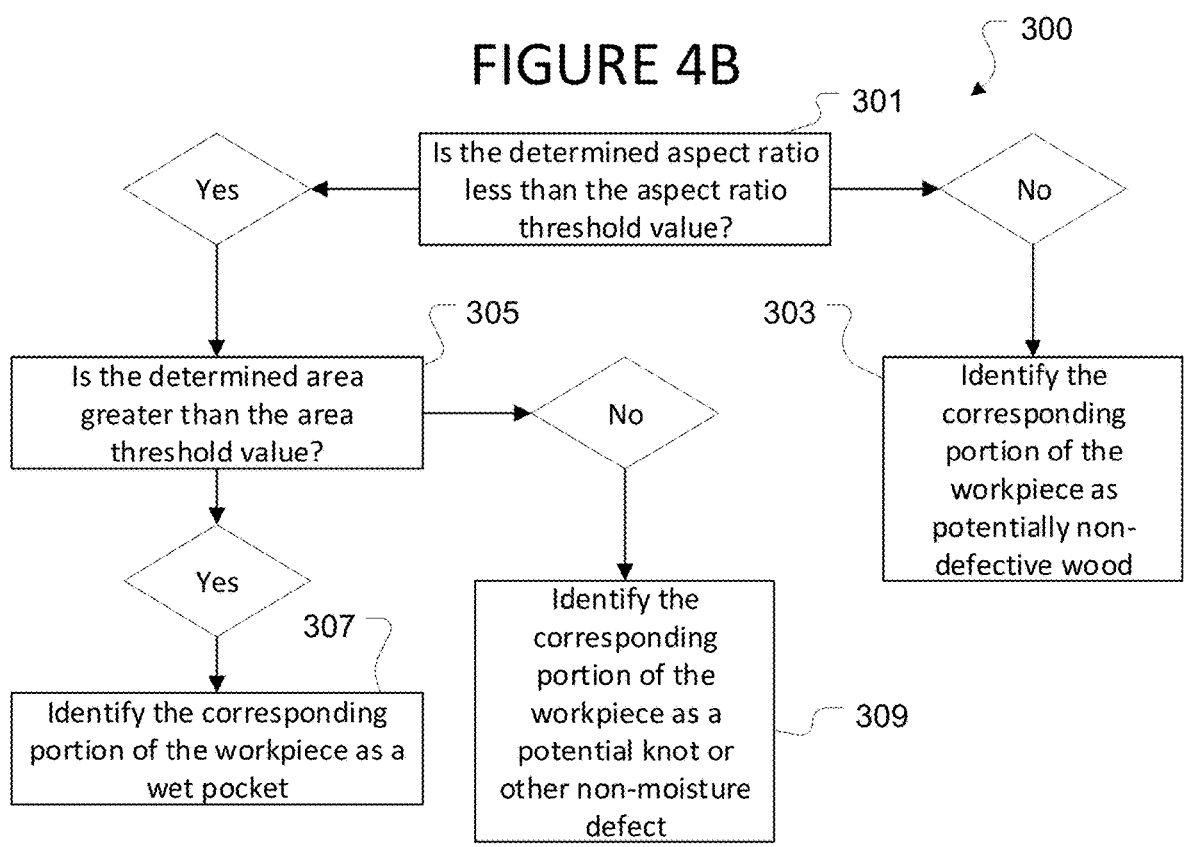
FIG. 4B is a flow diagram of a method of using image data to identify a wet spot.

In various embodiments, computer system 140 may be programmed to perform operations of a wet pocket detection method. FIGS. 4A and 4B illustrate an example of a wet pocket detection method 200 and a corresponding process flow 300, respectively. Optionally, one or more of the operations of method 200 and process flow 300 may be performed by scanner 130 and/or a sensor thereof. Although the description below refers to a laser spot in the singular for the sake of clarity, it is to be understood that multiple laser spots may be provided in a single image or multiple images and that each of the laser spots may be analyzed in the same or similar manner.

Referring now to FIG. 4A, method 200 may begin at block 201. At block 201, the computer system may determine an aspect ratio value and an area value of a laser spot based on an image of the laser spot. For example, the computer system may receive an image of the laser spot on the surface of the workpiece from a camera or scanner that is positioned to capture the image (e.g., camera 132). The computer system may determine an aspect ratio value and an area value for the laser spot based on the laser spot image data. The aspect ratio value may be a value that represents the ratio of the length of the laser spot to the width of the laser spot. Again, in some embodiments the laser spot image data may represent a plurality of laser spots, and the computer system may determine aspect ratio values and area values for some or all of the laser spots.

The aspect ratio and area values may be determined in any suitable manner. For example, the aspect ratio value for a laser spot may be determined by measuring the length of the laser spot along its major axis, measuring the width of the laser spot along its minor axis, and dividing the determined length by the determined width. As another example, in some embodiments the area of the laser spot may be determined according to the formula:

$$A = \pi ab,$$

where

'a' is the length of the semi-major axis (i.e., the radius of the laser spot along the major axis, equal to half of the length of the laser spot), and 'b' is the length of the semi-minor axis of the laser spot (i.e., the radius of the laser spot along the minor axis, equal to half of the width of the laser spot).

In some embodiments the area and aspect ratio of the laser spot may be determined as a function of the number or volume of pixels located at least partially within the image of the laser spot (e.g., pixels with intensity values that exceed a threshold intensity value). Alternatively, a best fit ellipse for the laser spot may be generated based on pixel intensity values (e.g., intensity values that exceed a threshold intensity value), and the aspect ratio and area values may be determined as a function of the number/volume of pixels within the best fit ellipse. In any case, the aspect ratio and area, or any parameters used to calculate aspect ratio and/or area (e.g., major, semi-major, minor, and/or semi-minor axes) may be measured in pixels, inches, millimeters, or any other suitable unit of measure. The values may be determined automatically by the computer system, the scanner, or the tracheid sensor/camera, or some combination thereof.

The computer system may use the aspect ratio value and the area value to generate an aspect ratio image and an area image, respectively, and analyze the two images (the 'tracheid channel images') to detect wet spots. For example, the computer system may generate an aspect ratio image of a workpiece, or a portion thereof, by converting the aspect ratio values of the respective laser spots to pixel values. Similarly, the computer system may generate an area image of the workpiece, or portion thereof, by converting the area values of the respective laser spots to pixel values. In some embodiments the pixel values may be greyscale pixel values. The conversion may be performed in any suitable manner. For example, a median or average expected value for the relevant parameter (aspect ratio or area) may be assigned a particular pixel value (e.g., a median value) within a pixel value range, and the actual values for that parameter may be converted to pixel values scaled to fit within that range. As another example, the highest actual value and the lowest actual value obtained for a given parameter may be assigned corresponding pixel values at the opposite ends of the pixel value range (e.g., 0 and 255, or vice versa). In some embodiments, the aspect ratio that represents the most circular laser spot shape may be assigned the highest pixel value in the desired pixel range (e.g., 255), the aspect ratio that represents the most elongated laser spot shape may be assigned the lowest pixel value in the desired pixel range (e.g., 0), and the largest and smallest areas may be assigned the highest and lowest pixel values in the desired pixel range, respectively. In that case, a wet spot would appear as a relatively bright region in both the area image and in the aspect ratio image.

Optionally, in some embodiments the computer system may use various processing techniques to correct or adjust the tracheid channel images before analyzing the images to detect wet spots. For example, to offset variability in response among sensor units (e.g., pixels) of the tracheid sensor(s), the computer system may adjust the intensity values of a portion (e.g., a row) of the tracheid channel image based on a typical intensity value for the corresponding pixel and a target intensity value (e.g., an average intensity value for normal wood). The computer system may also identify (e.g., flag) any portions of the tracheid channel images obtained by pixels that consistently return low intensity values (e.g., due to debris on the sensor lens) to exclude those portions from some or all further processing operations. Other embodiments may use other processing techniques to adjust the laser spot image data or tracheid channel images. Alternatively, these operations may be omitted and the computer system may use the tracheid channel images without adjusting those images or the corresponding values.

Optionally, at block 203, one or more additional values may be determined based on a second image of the surface of the workpiece. For example, in addition to receiving laser spot image data for a given surface portion of a workpiece, the computer system may receive color vision image data (e.g., from color vision camera 136) for the same surface portion of the workpiece. The computer system may analyze the color image data to aid in the identification of wet spots. For example, the computer system may process the color image data to identify regions of the image that are darker than a color threshold value (e.g., an average color of clear dry wood portions of that workpiece or other workpieces, etc.). Alternatively, block 203 may be omitted.

At block 205, a wet spot on the surface of the workpiece may be identified based at least on the aspect ratio value and area value. One example of a corresponding process flow 300 is illustrated in FIG. 4B, in accordance with various embodiments.

Referring first to FIG. 4B, at block 301 the aspect ratio value may be compared to an aspect ratio threshold value. The aspect ratio threshold value may represent the aspect ratio of a laser spot on clear wood. For example, the aspect ratio threshold value may be an average of aspect ratios of laser spots on portions of clear wood of the same workpiece and/or other workpieces. Alternatively, the aspect ratio threshold value may be a fixed value for a given wood species or batch of workpieces.

If the aspect ratio value is less than the aspect ratio threshold value, the process flow may proceed to block 305.

At block 305, the area value may be compared to an area threshold value. Again, the area threshold value may represent the area of a laser spot on clear wood. For example, the area threshold value may be determined as an average area of laser spots on portions of clear wood of the same workpiece and/or other workpieces. Alternatively, the area threshold value may be a fixed value for a given wood species or lot of workpieces.

If the area value is greater than the area threshold value, the corresponding portion of the workpiece may be identified as a wet spot (block 307). Optionally, if the area value is less than the area threshold value, the corresponding portion of the workpiece may be identified as a potential knot or another defect other than a wet spot (block 309). Alternatively, block 309 may be omitted.

While the above operations are illustrated in FIGS. 4A and 4B in a particular order, it is to be understood that any or all may be performed in a different order and/or repeated. For example, blocks 203, 205, and/or 207 may be performed in a different order or simultaneously. Likewise, blocks 301 and 305 may be performed in a different order or simultaneously one or more of the operations may be repeated, omitted, or performed out of order.

Some embodiments of the method may also include one or more additional operations. For example, if color vision data are used to aid in the identification of wet spots, the additional data may be analyzed at block 301 and/or block 305, and a wet spot may be identified at block 307 in response to determining that the aspect ratio value is less than the aspect ratio threshold value, the area value exceeds the area threshold value, and the color of the surface portion of the workpiece is darker than the color threshold. Optionally, the computer system may process the color image data before determining the respective values, such as by using various filtering, thresholding, scaling, and/or other image processing techniques to compress or simplify the data, eliminate inaccurate data, and/or compensate for missing or eliminated data.

As another example, in some embodiments the computer system may determine a laser spot angle value that represents the angle of the major axis of a laser spot relative to a reference axis (see e.g., FIG. 3B, reference axis 110), such as the direction of workpiece travel, or the longitudinal axis of the workpiece, or an axis that is coplanar with, and perpendicular to, the direction of workpiece flow. Optionally, the computer system may use the laser spot angle value in addition to the other determined laser spot values to identify a wet spot or confirm such an identification. For example, the computer system may confirm the identification (or increase a confidence value associated with the identification) of a wet spot based on a determination that the laser spot angles in that area of the workpiece surface are random. Alternatively, the computer system may not determine laser spot angle values or may determine and use such values for some purpose(s) other than for identifying wet spots. For example, computer system 140 may use laser spot angle values to identify or characterize grain angle, knots, and/or other workpiece characteristics.

In various embodiments, a wet spot detection system may be incorporated within a workpiece scanning system. For example, a lumber or veneer scanning system may be designed to include the tracheid sensor(s), computer system, and processing logic of a wet spot detection system. Alternatively, a wet spot detection system may be added to a pre-existing lumber scanning system or veneer scanning system as an upgrade. If the pre-existing scanning system includes at least one tracheid sensor (e.g., tracheid sensor 131), the wet spot detection system may be added by operatively coupling computer system 140 with the tracheid sensor(s). If the pre-existing scanning system has both a tracheid sensor and a computer system, the wet spot detection system may be added by providing the computer system with processing logic for performing some or all of the operations of a wet spot detection method described herein. In any case, the processing logic may be provided in the form of hardware (e.g. dedicated logic or circuitry), software (e.g., embodied on a non-transitory computer readable medium), or a combination of hardware and software. If the processing logic is provided in the form of software, the software may be provided as a computer program product available for download over a network (e.g., the internet) and/or from a remote source (e.g., a server, cloud storage, etc.) or on a computer-readable medium such as a machine-readable storage medium, random access memory, a magnetic disk or optical storage medium, a flash memory device, or other such item.

Thus, in various embodiments, a workpiece scanning system may include a wet spot detection system (e.g., wet spot detection system 100) with at least one tracheid sensor (e.g., tracheid sensor 131) and a computer system (e.g., computer system 140) with processing logic to identify a wet spot along a surface of a piece of wood based at least on data from the tracheid sensor(s). Optionally the lumber scanning system may further include one or more additional components, such as an additional sensor or light source, a scan frame, and/or means for moving workpieces through the scan zone(s).

Figure 5A:
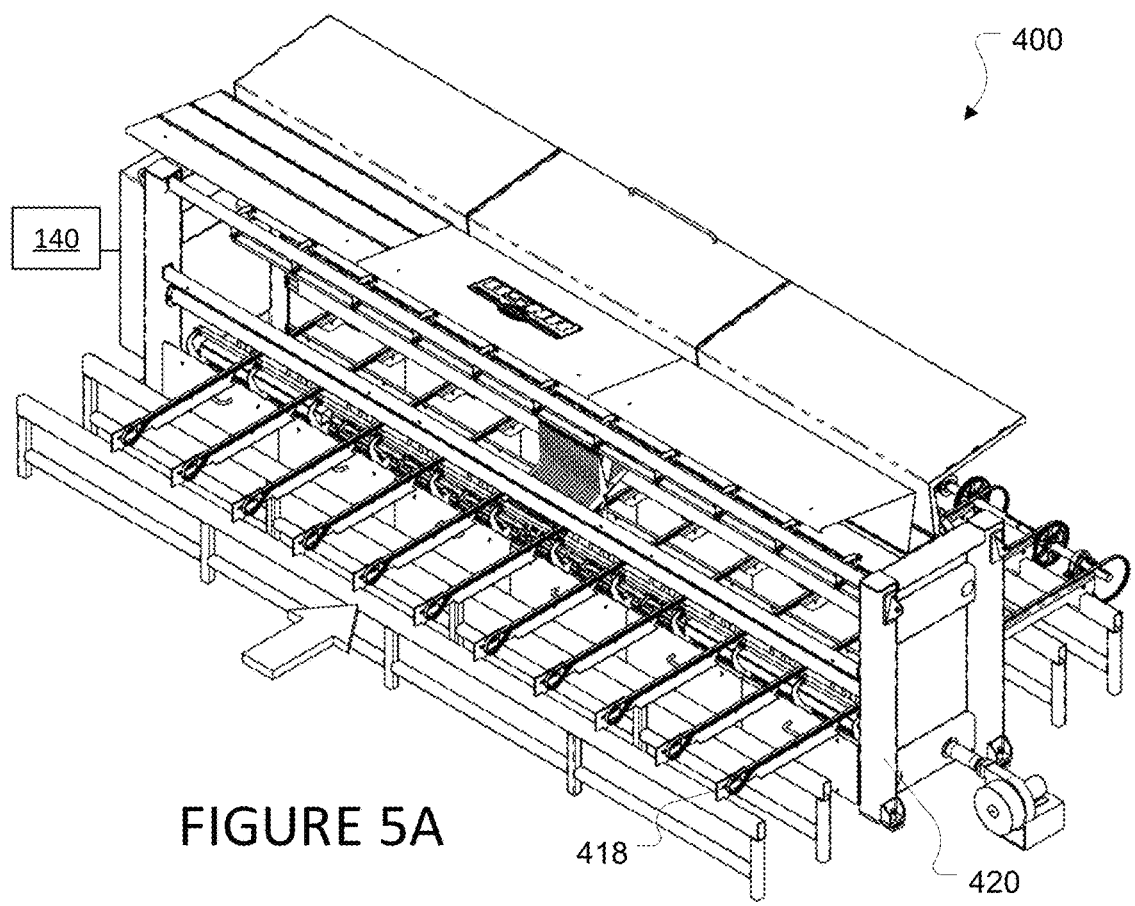
FIG. 5A is a perspective view of a scanner system that incorporates a wet spot detection system.
Figure 5B:
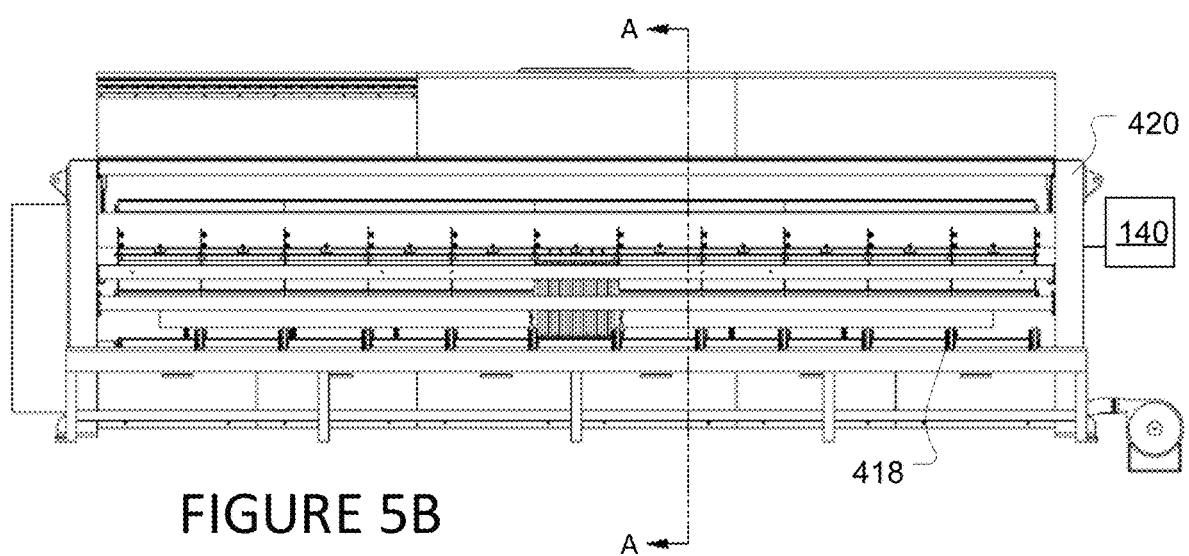
FIG. 5B is a front elevational view of the scanner system of FIG. 5A.
Figure 5C:
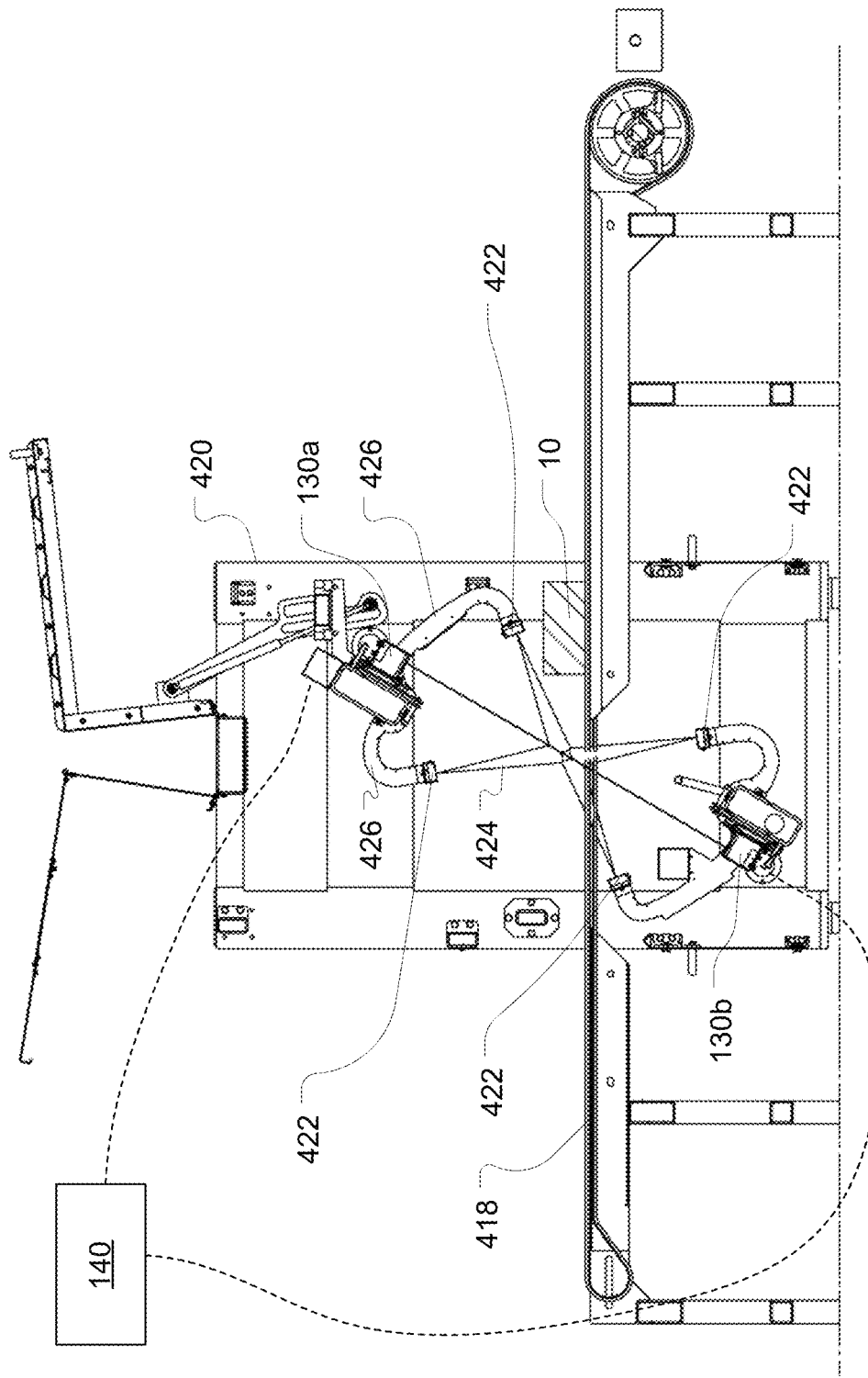
FIG. 5C is a sectional view of a transverse scanner system of FIGS. 5A-B, taken along the lines A-A of FIG. 5B.

FIGS. 5A-C illustrate perspective, front elevational, and sectional views, respectively, of a lumber scanning system with a wet spot detection system, in accordance with various embodiments.

Figure 5D:
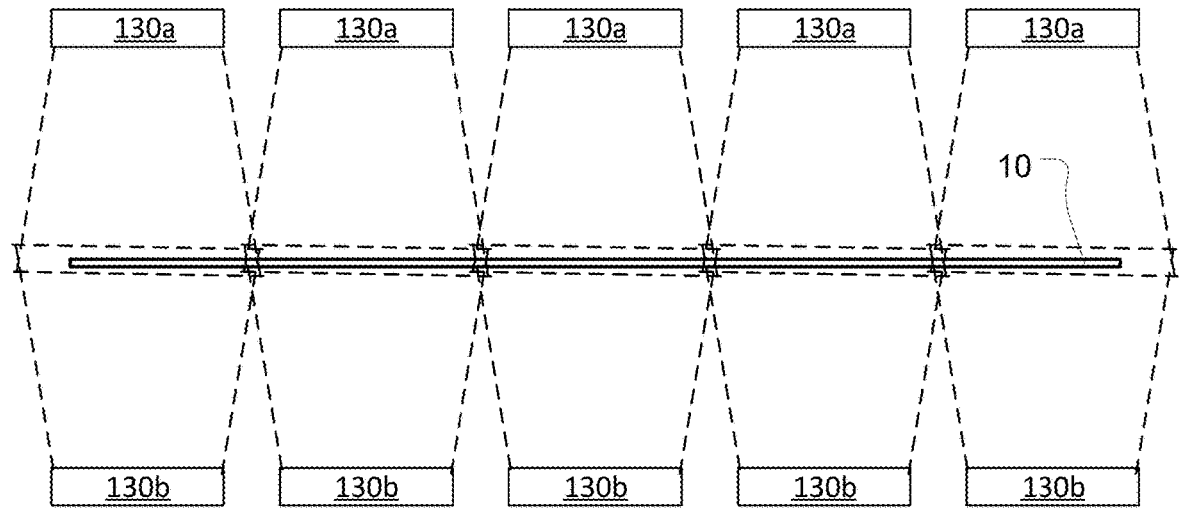
FIG. 5D is a schematic view of a scanner arrangement.

Referring first to FIG. 5C, lumber scanning system 400 may include a wet spot detection system (e.g., wet spot detection system 100) with a first group of scanners 130a, a second group of scanners 130b, and computer system 140. Optionally, the lumber scanning system 400 may further include a scan frame 420. Scan frame 420 may be positioned along a conveyor 418 that defines a path of workpiece flow. In this example, conveyor 418 is configured to convey workpieces (e.g., boards, flitches, or cants) through the scan frame in a transverse orientation (i.e., generally perpendicular to the direction of travel). The first and second groups of scanners 130a and 130b are arranged above and below the flow path, respectively, such that the fields of view of each group of scanners extends across the flow path, transverse to the direction of workpiece travel. In addition, scanners 130a and 130b are positioned off-axis to enable each of the respective cameras to capture images of a corresponding face and side of each workpiece. Optionally, the scanners of each group may be arranged such that the fields of view overlap to some extent (see e.g., FIG. 5D).

Figure 6:
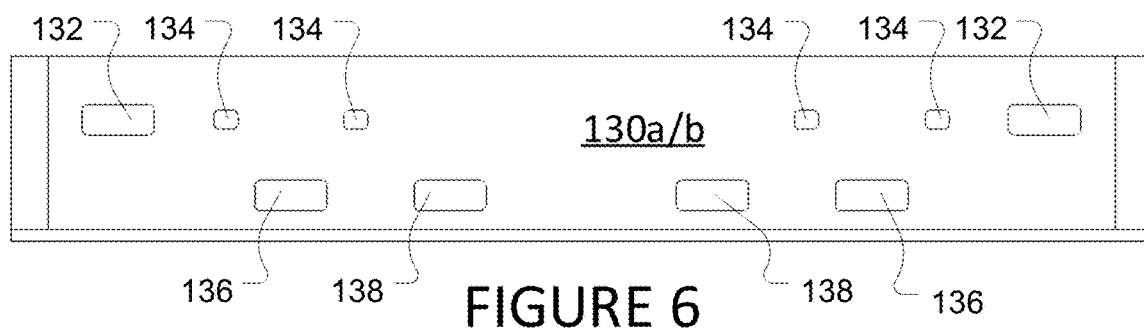
FIG. 6 illustrates an example of a scanner suitable for use in a wet spot detection system.

In this embodiment, each of the scanners 130a and 130b includes a pair of tracheid sensors 131, a pair of color vision cameras 136, and a pair of laser profile sensors 138 (FIG. 6). The scanners are mounted to, and located generally within, the scan frame 420. Arrays of light sources 422 are positioned both upstream and downstream of each group of scanners. For example, the light sources 422 may be mounted to support arms 426 which are in turn mounted to the scan frame 420. Optionally, support arms 426 may be adjustable to reposition light sources 422. Regardless, the light sources may be positioned to project light onto the surfaces to be imaged by the respective color vision cameras 136.

Figure 7:
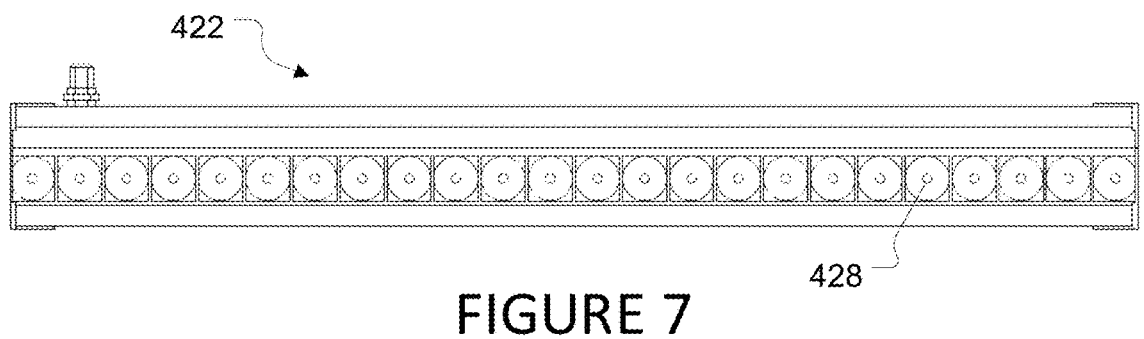
FIG. 7 illustrates an example of a light source suitable for use in a wet spot detection system.

In some embodiments each light source 422 may include LED lights 428 (FIG. 7) arranged in one or more rows. Alternatively, light sources 422 may be another type of light source, or a combination of different types of light sources. In some embodiments the light sources 422 may be omitted. Similarly, in some embodiments the scan frame may be omitted, and the scanner(s) 130 and/or light sources 422 may instead be mounted to other support means, such as the frame of the conveyor or a floor, ceiling, wall, or other structural component of the facility or any of the equipment therein.

In various embodiments, the scanner(s) 130 may be arranged in any suitable manner to scan workpieces as they are moved along a path of flow. The scanner(s) may be arranged to scan workpieces traveling in a transverse orientation, or to scan workpieces traveling in a lineal orientation. Likewise, if the lumber scanning system has multiple scanners or groups of scanners, some of the scanners may be spaced apart along the direction of workpiece travel. In any case, the scanners may be positioned off-axis, or positioned on-axis, or some may be positioned off-axis and others may be positioned on-axis.

In operation, as the workpiece is transported through the scan frame 420 on the conveyor 418, the laser light sources 134 project laser beams onto the workpiece and cameras 132 capture images of the resulting laser spots on the workpiece.

The color vision cameras 136 capture color images of the same surface(s) of the workpiece. Optionally, the color vision cameras 132 and light sources 422 of a group of scanners may be operated to alternate with the corresponding tracheid sensors 131 of the same scanners. Alternatively, the color vision cameras 132 and respective light sources 422 may be positioned upstream or downstream of the tracheid sensors to avoid interference between light sources. In that case, the color vision cameras and tracheid sensors may be operated either simultaneously or in an alternating manner.

The scanners 130 may send the laser spot image data and the color vision image data for a given workpiece surface (e.g., a face or a longitudinal side of a board or flitch) to computer system 140. The computer system may be programmed with sensor logic and wet pocket detection logic. The computer system 140 may use the tracheid sensor image data and the color image data to identify wet spots, if any, along the imaged surface of the workpiece.

Figure 8:
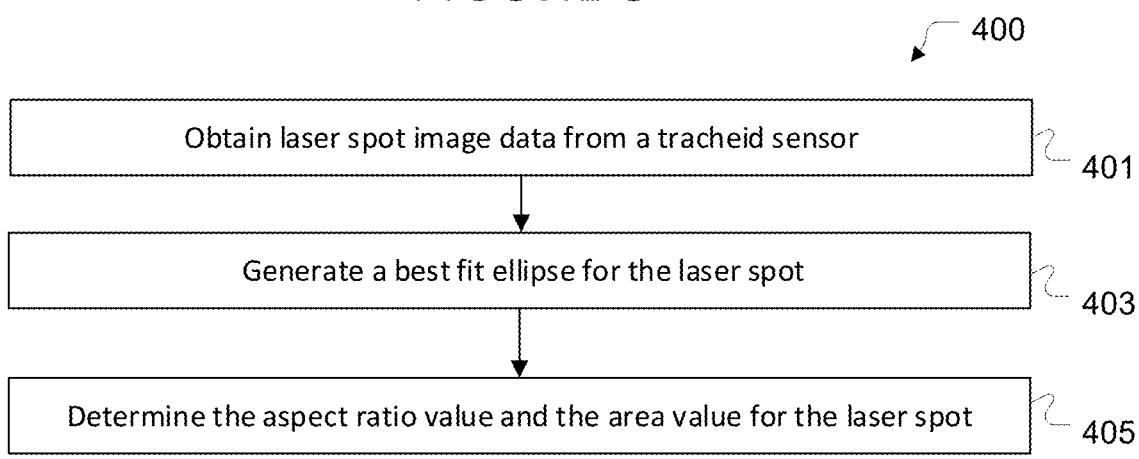
FIG. 8 is a flow diagram of a process for determining an aspect ratio value and an area value for a laser spot.
Figure 9:
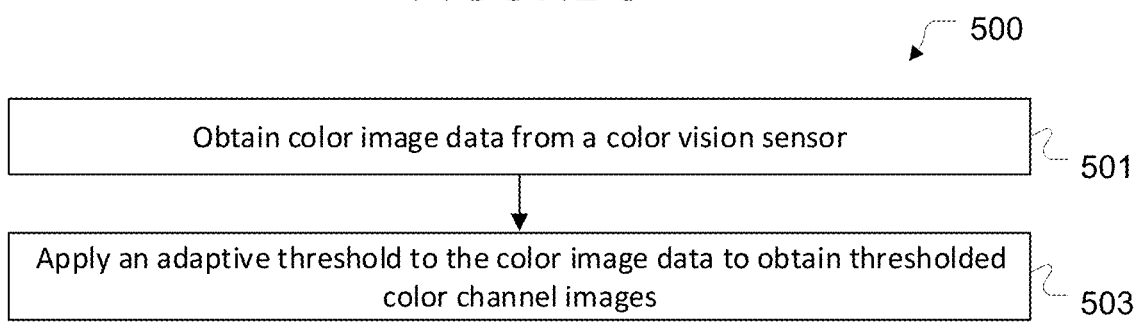
FIG. 9 is a flow diagram of a process for obtaining color image data.
Figure 10:
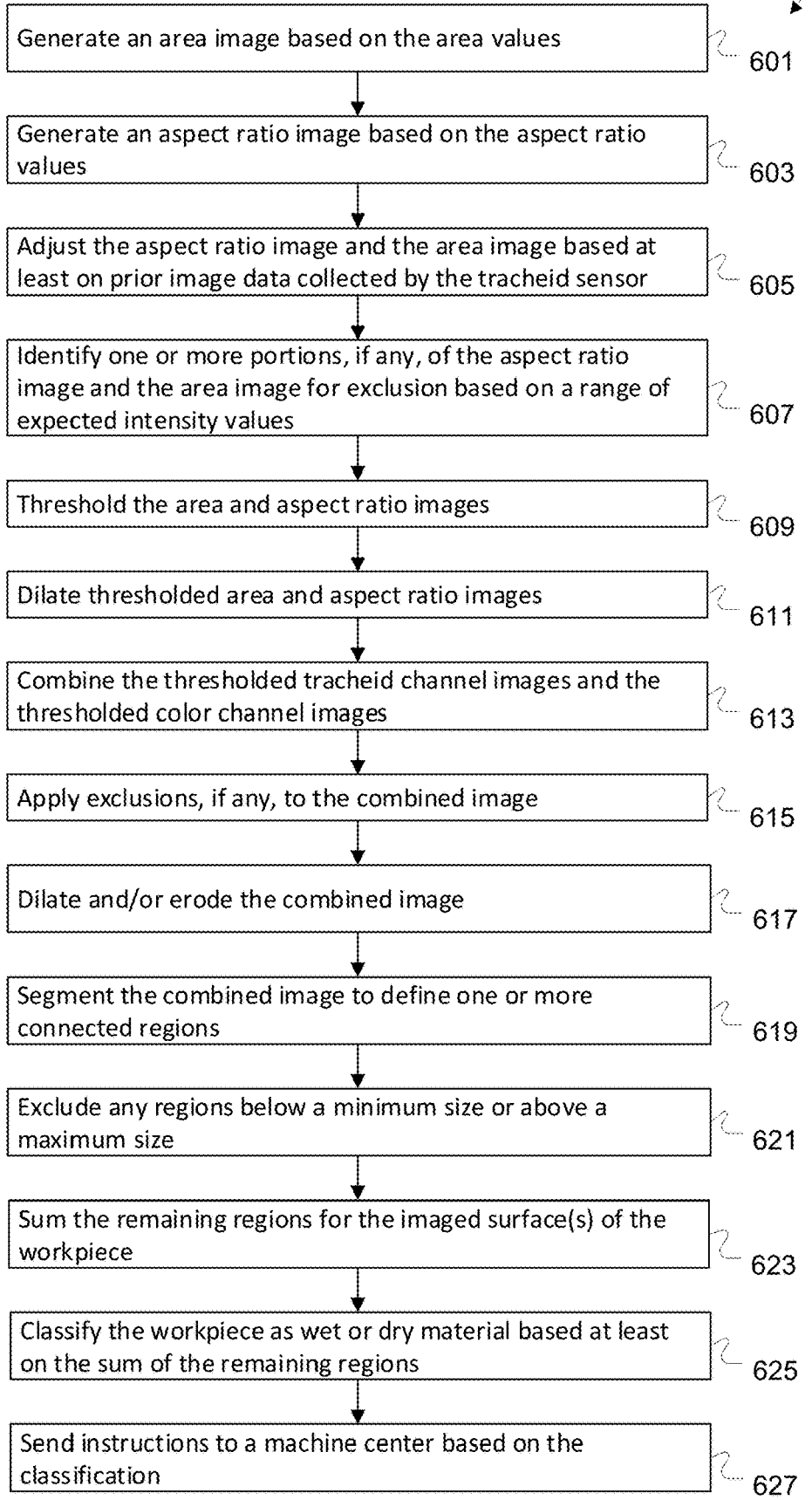
FIG. 10 is a flow diagram of a method of using image data to identify a wet spot.

FIGS. 8-10 illustrate an example of a particular implementation of method 200 in a transverse scanning system (e.g., scanning system 400). For clarity, this embodiment of the method may include any or all of the operations, processes, techniques, features, and other aspects described above with reference to method 200. Again, while portions of the following description refer to a laser spot in the singular, those with ordinary skill in the art will appreciate that the method may be used to analyze multiple laser spots on multiple surfaces of a workpiece. In addition, any or all of the various operations described herein as operations performed by the computer system may instead be performed by the respective camera(s), sensor(s), and/or scanners.

Returning briefly to FIG. 4A, at block 201 the computer system may determine an aspect ratio value and an area value of a laser spot based on an image of the laser spot. A corresponding process flow 400 is illustrated in FIG. 8.

At block 401, the computer system may receive a raw image of the laser spot on the surface of the workpiece from the tracheid sensor. The computer system may process the raw image to identify the laser spot in the image. Optionally, the computer system may threshold the raw image to distinguish foreground (the laser spot) from background (the surrounding surface portion of the workpiece) based on pixel intensity values. Alternatively, the computer system may distinguish the laser spot from the surrounding area using any other suitable technique.

Optionally, at block 403 the computer system may generate a best fit ellipse for the laser spot. For example, a best fit ellipse for the laser spot may be generated based on pixel intensity values (e.g., intensity values that exceed a threshold intensity value). Image processing techniques and algorithms for identifying the contours of laser spots in tracheid images and generating a best fit ellipse are well known in the art, and are therefore not described in further detail herein.

At block 405 the computer system may determine the aspect ratio value and the area value for the laser spot. If the computer system generates a best fit ellipse at block 403, the computer system may determine the aspect ratio and area values based at least in part on the best fit ellipse. For example, a best fit ellipse for the laser spot may be generated based on pixel intensity values (e.g., intensity values that exceed a threshold intensity value), and the aspect ratio and area values may be determined as a function of the number/volume of pixels within the best fit ellipse. Alternatively, block 403 may be omitted and the computer system may determine the aspect ratio and area values based on the image of the laser spot (as opposed to the best fit ellipse). In any case, the aspect ratio and area, or any parameters used to calculate aspect ratio and/or area (e.g., major, semi-major, minor, and/or semi-minor axes) may be measured in pixels, inches, millimeters, or any other suitable unit of measure.

Optionally, the computer system may also process the tracheid sensor image data to extract an angle value for the laser spot. Each type of laser spot value may be considered a separate tracheid channel. Thus, in some embodiments the laser spot values may collectively constitute two separate channels (aspect and area). In other embodiments, the laser spot values may collectively constitute three separate channels (aspect ratio, area, and angle). The computer system may convert the aspect ratio values and the area values to corresponding pixel values to generate an aspect ratio image and an area value image, respectively.

Again, in other embodiments some or all of the operations of process flow 400 may be performed by the tracheid sensor camera, the tracheid sensor, and/or the scanner. For example, in some embodiments the tracheid sensor camera, the tracheid sensor, or the scanner may include sensor logic configured to assemble line scan or area scan image data into an image of the workpiece surface and to determine the aspect ratio and area values based on the image.

Referring again to FIG. 4A, at block 203 the computer system may optionally determine one or more additional values based on a second image of the surface of the workpiece. FIG. 9 illustrates a corresponding process flow 500.

At block 501, the computer system may obtain a color image of the same surface of the workpiece from a color vision sensor (e.g., color vision sensor 136). The color image may represent three channels of color vison data (e.g., red, green, and blue channels).

At block 503, the computer system may apply an adaptive threshold to the color image data to obtain processed color channel images. The computer system may process all three of the color channels independently to create background images and may use the background images as a basis for determining a threshold value. The computer system may use adaptive threshold logic to compute a local average intensity value by excluding any extreme (high or low) intensity values. This value may be scaled and applied to the color channels, and pixels with intensity values that exceed this value are thresholded for further processing. Examples of a color vision image of a workpiece and corresponding thresholded color channel images (red, green, and blue channels) are shown in FIGS. 11A, 11B, 11C, and 11D, respectively. Again, in some embodiments some or all of these operations may be performed by the color vision sensor and/or the respective scanner.

Specifically, at block 503 the computer system may use each channel of color image data to generate a corresponding color channel image. The computer system may analyze each of the color channel images to identify any pixel intensity values that are outside of an expected range of intensity values (e.g., an expected range for defect-free wood). The expected range may be set by an operator. Alternatively, the expected range may be determined automatically by the computer system based on image data (e.g., a histogram of the respective image, historical image data statistics, etc.). Preferably the expected range is one that excludes at least some pixel intensity values typically associated with relatively dark defects, such as cracks and dark knots, but includes pixel intensity values typically associated with defect-free wood. For example, a range of 20-235 may be suitable for some softwood species (e.g., those with relatively dark heartwood and light sapwood). The computer system may calculate a threshold value for the color channel images by calculating the average of the pixel intensity values that are within the expected range. In some embodiments the computer system may calculate an average intensity value for each color channel image separately, using the intensity values from each image to determine the average intensity value for that image. Alternatively, the computer system may determine one average intensity value for all three of the color channel images based on the intensity values of all three. In any case, the average intensity value may represent an average intensity of clear wood (straight-grained and defect-free) surface portions of that workpiece. The computer system may scale and apply the average intensity value(s) to the color channel images as a threshold value(s) to generate binary color channel images. For example, the computer system may assign a first pixel value (e.g., 0) to the pixels with intensity values that were equal to or greater than the threshold value, and assign a second pixel value (e.g., 255) to pixels with intensity values that were less than the threshold value (see e.g., FIGS. 11B-D).

Returning again to FIG. 4A, at block 205 the computer system may identify a corresponding portion of the workpiece as a wet spot based at least on the aspect ratio value and the area value. A corresponding process flow 600 is illustrated in FIG. 10.

Figures 14A, 14B, 14C:
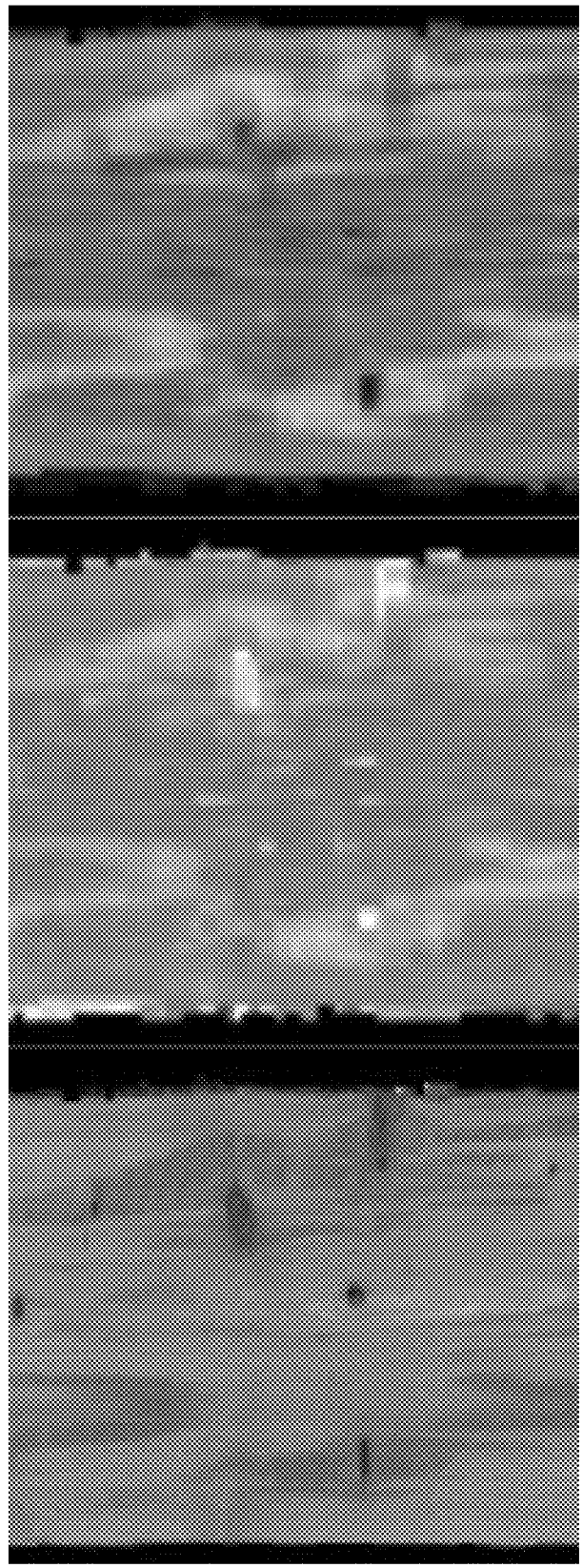
FIGS. 14A-C show a color (RGB) image, a tracheid channel aspect ratio image, and a tracheid channel area image, respectively, of a workpiece.

Referring now to FIG. 10, the computer system may generate an area image based on the area values (block 601) and generate an aspect ratio image based on the aspect ratio values (block 603). Again, in some embodiments the computer system may generate these images by converting the respective values (the aspect ratio values and area values of the respective laser spots) to greyscale pixel values. For example, the computer system may determine, or may be provided with, expected area and aspect ratio values. These values may represent the expected area and aspect ratio, respectively, of a laser spot on non-defective straight-grained dry wood. The expected area and aspect ratio values may be assigned a pixel value of 128, and the actual values may be converted to pixel intensity values within a possible or desired range (e.g., 0 to 255) as a function of the difference between actual and expected value. In that case, a wet spot may appear as a relatively bright region in both the area image and the aspect ratio image. Examples of a color image of a workpiece and corresponding aspect ratio and area images are shown in FIGS. 14A, 14B, and 14C, respectively.

Optionally, at block 605 the computer system may adjust the aspect ratio image and/or the area image based at least on prior image data collected by the respective tracheid sensor(s). In some embodiments, the computer system may have tracheid channel calibration logic configured to equalize the outputs from individual sensor units and/or correct image distortions caused by lens contaminations, which may help to produce a more uniform and consistent image.

Figures 15A, 15B:
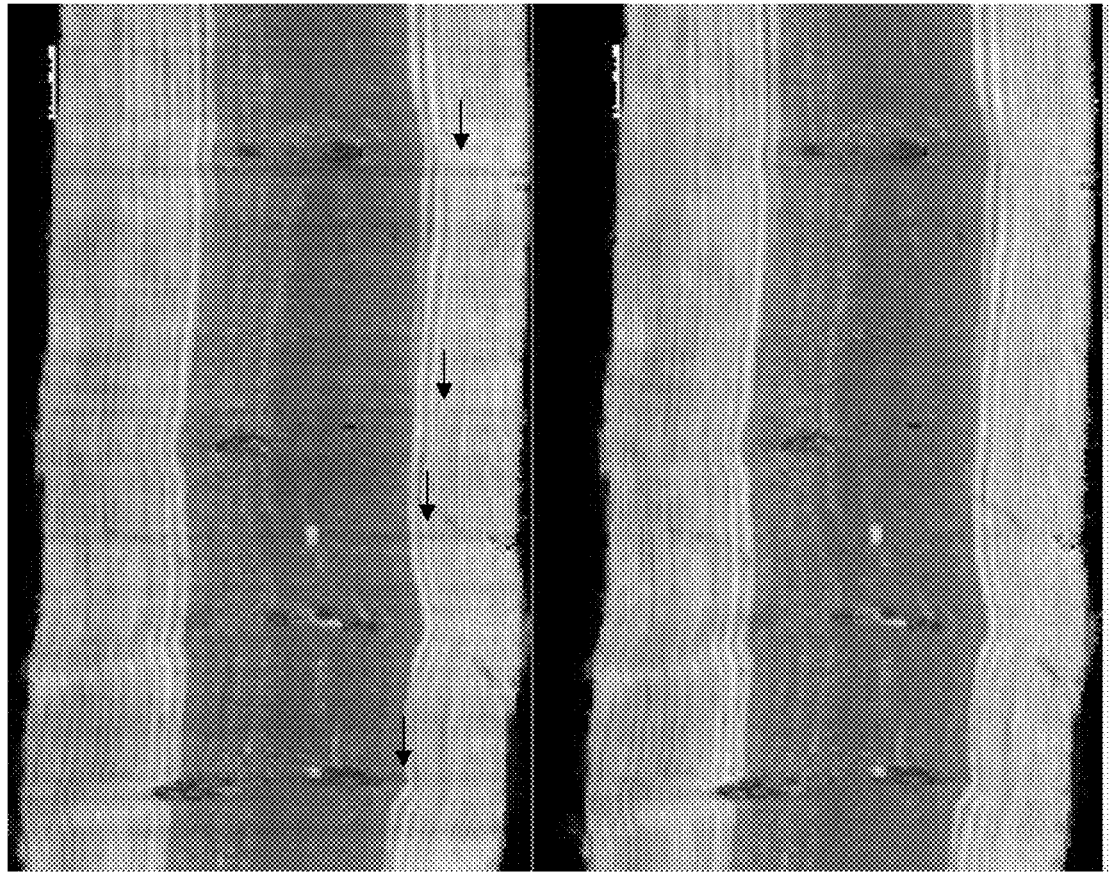
FIGS. 15A-B show uncorrected (15A) and corrected (15B) tracheid channel area images.

The tracheid correction logic may use sensor pixel statistics to correct image intensity values. For example, in a transverse scanning arrangement, the image of the laser spot(s) on the surface of the workpiece may be collected by a linear sensor array (e.g., cameras 132a/132b) arranged across the path of flow, perpendicular to the direction of workpiece travel. The linear sensor array includes a plurality of sensor units (e.g., pixels or other photosensitive elements of cameras 132a/132b) with fields of view that fan out across the flow path to cover corresponding areas along the length of the workpiece. The fields of view of adjacent sensors and/or sensor units may overlap to some extent (see e.g., FIG. 5D). Due to the arrangement of the sensor units and the overlapping fields of view, there may be some variability in sensor unit responses along the operational range of the array. If a certain pixel consistently collects lower (or higher) intensity values than other pixels, the area image (and possibly the aspect ratio image) may have a corresponding streak that extends in the direction of workpiece travel. For example, if a pixel consistently collects lower values than other pixels in response to a given light stimulus, the corresponding portion (row) of the raw image will have lower pixel intensity values than other portions of the image. Because the intensity of a laser spot tends to decrease as a function of distance from its center, the edges of the laser spots in that portion of the raw image may be more difficult to detect against the background of the image, which may cause the computer system to calculate smaller area values for those laser spots. Thus, when the area image is generated, the corresponding row may appear darker than adjacent rows, which appears as a streak across the image. In a transverse scanning embodiment, the streak would be generally transverse to the length of the workpiece, whereas in a lineal scanning embodiment, the streak would be generally parallel to the length of the workpiece. FIG. 15A shows an uncorrected area image of a workpiece that was scanned in a transverse orientation, with arrows indicating some of the streaks resulting from variability in pixel responses.

To compensate for this type of sensor variability, the correction logic may sample image intensity as the workpiece travels, collecting statistics for each pixel location (row of the image). Pixel row statistics may be collected as, or converted to, image intensity histograms. The histograms may be analyzed for consistently low or high values. Various measures, such as histogram mode, percentile, and/or average, may be extracted to determine a typical intensity value for a pixel row. The typical intensity value and an intensity target value may be applied to a correction equation to calculate a correction coefficient for that pixel. The intensity target value may be an average intensity value for clear (defect-free) wood of one or more wood species. For example, the computer system may have one intensity target value for softwood species and another intensity target value for hardwood species. Various correction equations can be used, including linear slope, offset, and slope and offset. A non-linear correction, such as cubic ($y=a*x2+b*x+c$), can be also be applied. The correction equation may be used to calculate a correction coefficient for each pixel, and the correction coefficients may be applied to the area and aspect ratio images to adjust the intensity values of the images. FIG. 15B shows a corrected area image produced by using the above-described tracheid correction logic to adjust the area image shown in FIG. 15A.

The tracheid correction logic may sample image intensity continuously during operation of the scanner(s). In some embodiments, the tracheid correction logic may recalculate the correction coefficients upon collecting a predetermined number of pixel intensity values (e.g., 2,000-10,000 pixel intensity values) per pixel row. In other embodiments, the tracheid correction logic may recalculate the correction coefficients for each successive workpiece, and/or at predetermined intervals of time. Alternatively, the tracheid correction logic may recalculate the correction coefficients less frequently to reduce burden on system processing time. In any case, after correction coefficients are recalculated the histograms may be reduced (e.g., by excluding or discarding older pixel intensity data) to reduce the effect of the statistics history, in order to increase the weight of the new data while gradually diminishing the effect of the older data. Because of this demand on large statistics, the tracheid correction logic may be relatively slow to react to sensor changes. For example, in some embodiments the tracheid correction logic may respond to sensor changes within 100-1000 scanned workpieces.

Figures 16A, 16B:
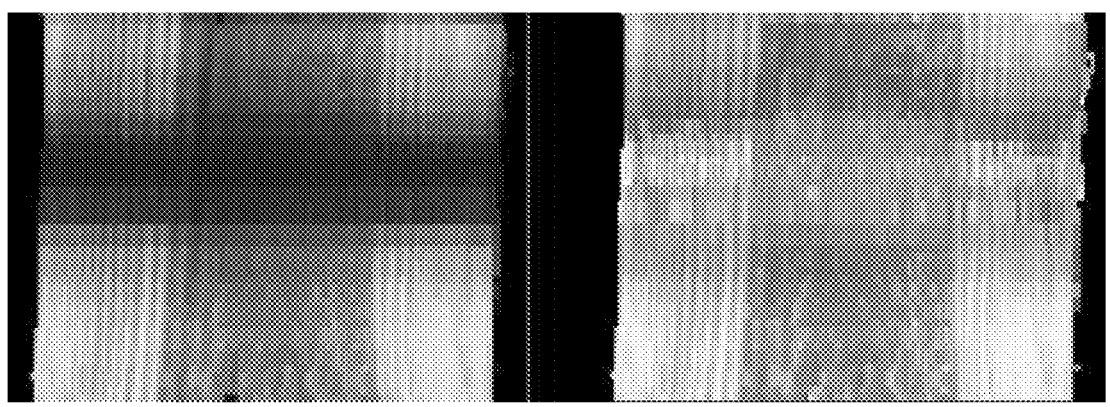
FIGS. 16A-B show sensor lens contamination causing low pixel values for a tracheid channel area image (16A) and high pixel values for a tracheid channel aspect ratio image (16B)

Optionally, at block 607, the computer system may identify one or more portions (if any) of the aspect ratio and area images for exclusion based on a range of expected intensity values. For example, in some applications sensor lens contamination can be a major source of image variability. This contamination can be difficult to avoid in sawmills and planer mills, and tracheid channels are particularly sensitive to sensor contamination. Sensor lens contamination may happen suddenly, such as from sawdust or a wood chip falling onto a sensor lens below the flow path. The tracheid correction logic may be relatively slow to react to such events, and/or may be unable to offset the effect of serious contamination events (e.g., a wood chip obstructing a camera lens). FIGS. 16A and 16B show examples of tracheid channel images in which the contamination of a sensor lens resulted in low pixel intensity values for the area channel (FIG. 16A) and high pixel intensity values for the aspect ratio channel (FIG. 16B). Therefore, in some embodiments the computer system may have tracheid monitoring logic configured to detect sensor lens contaminations quickly and respond to contamination events (e.g., by identifying the affected portion(s) of the image for exclusion) that cannot be handled or offset by the tracheid calibration logic.

Like the tracheid correction logic, the tracheid monitoring logic may collect intensity statistics for every pixel row of the image. However, instead of simply sampling the intensity statistics, the tracheid monitoring logic may analyze the tracheid sensor image data for each workpiece to identify intensity values that are outside of a range expected for defect-free wood. The tracheid monitoring logic may determine, for each workpiece, the percentage of pixels that are outside of the expected range. The tracheid monitoring logic may track the percentages to determine whether they exceed a predetermined percentage (e.g., an expected out-of-range percentage) for a specified number of workpieces (e.g., 5 to 50 workpieces). In response to determining that the out-of-range percentages for the specified number of workpieces exceed the predetermined percentage, the tracheid monitoring logic may determine that a sensor area is contaminated.

In some embodiments, the computer system may issue an alarm to notify a machine operator of the problem and its location. For example, the computer system may send instructions to an output device (e.g., a computer monitor, a touchscreen, a projector, etc.) to cause the output device to display an image or other type of message that identifies the affected scanner or portion thereof to a human operator. In some embodiments, in response to determining that a sensor area is contaminated, the computer system may identify the affected image rows as unusable for another operation or analysis that would otherwise use that data. For example, the computer system may flag the affected image rows, and defect detection logic (described further below) may to skip over or interpolate over the flagged area(s). This may help to reduce false positive defect identifications in areas of the workpiece that do not have those defects. In some embodiments, the computer system may issue an alarm and may also flag the affected data in response to determining that a sensor is contaminated.

In some embodiments, each new set of workpiece statistics (e.g., percentage of pixels out of the expected range for a given workpiece) may replace the oldest set of workpiece statistics in the pixel row history. This may help to eliminate long term history effects (e.g., by reducing the weight of old data relative to newer data) and/or enable the computer system to react more quickly to sensor contamination events (e.g., by setting and resetting pixel row flags as sensors become contaminated or are cleaned to remove the contaminant).

At block 609 the computer system may threshold the area image and the aspect ratio image. In some embodiments, the defect detection logic may apply a fixed threshold to the two tracheid channels (i.e., to the laser spot area channel and the laser spot aspect ratio channel). The same fixed threshold may be applied to both of the tracheid channels. Alternatively, one threshold may be applied to one of the tracheid channels and a different threshold may be applied to the other. Regardless, pixels with intensity values that exceed the relevant threshold may be replaced with pixels of one value (e.g., 255/white) and the remaining pixels may be replaced with pixels of another value (e.g., 0/black), resulting in binary images.

At block 611 the computer system may dilate the thresholded area and aspect ratio images to obtain processed area and aspect ratio images. The area and aspect ratio images may be dilated separately to fill in gaps and/or to enlarge regions of interest in the images. FIG. 12A shows the color image of FIG. 11A, and FIGS. 12B and 12C show corresponding aspect ratio and area images, respectively, that have been thresholded and dilated.

At block 613 the computer system may combine the processed color channel images and the processed area and aspect ratio images to obtain a combined image. In some embodiments, the processed color channel, area, and aspect ratio images are binary images and the defect detection logic may combine them with AND operation. In the resulting combined image, the intensity value of each pixel may be assigned one of two values based on the intensity value of the corresponding pixel in each of the processed images. For example, pixels in the combined image may have a first intensity value (e.g., 255) only if the corresponding pixel(s) in all of the processed images have that pixel intensity value, and the remaining pixels of the combined image may have the second intensity value (e.g., 0). As a result, foreground regions of the combined image may represent portions of the workpiece surface that were relatively dark in color and in which the laser spots were relatively large and relatively round. FIG. 12D shows a combined image produced by combining the images of FIGS. 11B, 11C, 11D, 12B, and 12C with AND operation. Alternatively, the processed color channel, area, and aspect ratio images may be combined using any other suitable technique.

Optionally, at block 615 the computer system may apply one or more exclusions to the combined image. Examples of exclusions include, but are not limited to, knots, wane, and workpiece edges. In some embodiments, the computer system or defect detection logic may be configured to identify a defect (e.g., a knot, wane, workpiece edge, rot, stain, or other defect) and to assign the second (background) intensity value to the pixels within a corresponding portion of the combined image. In embodiments in which the computer system has tracheid monitoring logic, the computer system may optionally exclude any portions of the combined image that correspond to flagged portions of the area image and/or aspect ratio image. FIG. 13A shows the color image of FIGS. 11A and 12A, and FIG. 13B shows an image of two exclusions for knots detected along the surface of the workpiece. Other embodiments may omit block 615. In still other embodiments, block 615 may be performed only if particular defects (e.g., knots, wane, and/or edges) are detected on that workpiece. If block 615 is omitted, the method may proceed from block 613 to 617.

Optionally, at block 617 the computer system may dilate and/or erode the resulting combined image. For example, the computer system may perform one or more dilation and/or erosion operations to fill in gaps and/or enlarge regions of interest in the combined image. FIG. 13C shows an image obtained by applying the exclusions of FIG. 14B to the combined image shown in FIG. 12D, followed by dilation/erosion of the resulting image. If block 617 is omitted, the method may proceed from block 615 (or from block 613, if block 615 is also omitted) to block 619.

At block 619 the computer system may segment the combined image to define one or more connected regions. In some embodiments, the computer system may exclude any regions below a minimum size and/or any regions above a maximum size. For example, the computer system may compare the sizes of the connected regions to pre-determined maximum and minimum sizes, exclude any connected regions that are larger than the maximum size, and exclude any connected regions that are smaller than the minimum size. The maximum and minimum sizes may be stored in a memory, accessed from a server, entered as input by a human operator, or received from another computer. Alternatively, the computer system may be programmed to determine the maximum and minimum sizes based on a training dataset (e.g., binary images of workpieces with and without wet spots) through conventional machine learning techniques. Optionally, the computer system may perform other operations at block 619 to further define any remaining regions.

Optionally, at block 621 the computer system may exclude any regions below a minimum size and/or above a maximum size. In some embodiments, an operator may set the minimum size and/or maximum size.

At block 623 the computer system may sum the remaining regions in the image. The remaining regions may represent wet spots on a corresponding surface portion of the workpiece. In some embodiments, images of multiple surfaces of the workpiece (e.g., both faces, or faces and sides) and/or multiple surface portions (e.g., different portions of the same face) may be obtained and analyzed as described above, and the computer system may sum the remaining regions in some or all of the corresponding images of the workpiece. For example, in some embodiments the computer system may have grade determining logic that combines the detected wet spots from different surfaces (e.g., top and bottom faces) of the workpiece. The grade determining logic may sum all of the wet spots (e.g., the areas of all of the remaining connected regions) in the corresponding images of those surfaces.

At block 625 the computer system may classify the workpiece as wet material or dry material based at least on the sum of the remaining regions. In some embodiments the computer system may determine a wet spot value based at least in part on the sum of the remaining regions and compare the wet spot value to a classification threshold value to classify the workpiece as wet material or dry material.

In some embodiments the wet spot value may be the sum of all of the wet spots detected on the surface(s) of the workpiece or portion thereof (i.e., the sum of the areas of all of the remaining connected regions in the corresponding image(s)). Alternatively, the wet spot value may be a ratio, percentage, or other value that represents the area of the wet spots relative to the total area of the corresponding workpiece surface(s). For example, the computer system may sum the areas of all of the wet spots (remaining connected regions) in all of the corresponding images of the workpiece to obtain a total wet spot area value, and the computer system may determine the wet spot value as a ratio of the sum of the areas of all of the wet spots detected on the surface(s) of the workpiece to the area of the surface(s), or as a corresponding percentage.

In other embodiments, the wet spot value may represent an estimated volume of wet pockets. For example, in some such embodiments the computer system may detect wet spots on multiple surfaces of the workpiece (e.g., opposite faces of a board or flitch), generate a 3D model of the workpiece that indicates the detected wet spots on the workpiece surfaces (or alternatively, alter or update an existing 3D model of the workpiece to indicate the detected wet spots), and analyze the 3D model to estimate the volume of the wet pocket(s). For instance, if two wet spots are located on opposite faces of the workpiece and are generally aligned along an axis orthogonal to the faces, the computer system may assume that the wet spots are sections of a wet pocket that extends through the workpiece. In that case, the computer system may estimate the volume of the wet pocket based at least in part on the sizes and shapes of the detected wet spots and the thickness of the workpiece (distance between the faces). If a wet spot is detected on one face and no wet spot is detected in a corresponding area of the opposite face, the computer system may assume that the detected wet spot is a section of a wet pocket that does not extend through the workpiece. In such cases, the computer system may estimate the volume and/or 3D shape of the wet portion based on the size and shape of the detected wet spot and the thickness of the workpiece or some fraction thereof (e.g., half of the thickness, a quarter of the thickness, a tenth of the thickness, etc.). Alternatively, the computer system may estimate the volume of wet pockets in any other suitable manner, such as by using known techniques for estimating the volume of other defects. For example, the computer system may estimate the volume of wet pockets by applying known techniques for estimating the volume of a knot based on vision image and/or geometric data. Regardless, if the computer system estimates the volume of wet pockets within the workpiece, the computer system may determine the wet spot value as a sum of all of the estimated volumes of the wet pockets, or as a ratio of that sum to the total volume of the workpiece, or a corresponding percentage.

In response to a determination that the wet spot value exceeds the classification threshold value, the computer system may classify the workpiece as wet material. In response to a determination that the wet spot value does not exceed the classification threshold value, the computer system may classify the workpiece as dry material. Optionally, the computer system may indicate the classification in an electronic record associated with the workpiece. For example, in some embodiments the computer system may add the classification to an electronic record that includes other information about the workpiece (e.g., dimensions, species, defect information, grade, etc.). As another example, in some embodiments the computer system may create or update a virtual model of the workpiece that indicates the sizes and locations of the wet spots.

Optionally, at block 627 the computer system may send one or more instructions to a machine center based at least in part on the classification. For example, in some embodiments, in response to classifying the workpiece as wet material, the computer system may send a signal to a sorting device (e.g., a drop-out gate, a feed roll or positioning roll, a diverter, etc.) to cause the sorting device to change the path of travel of the workpiece. As another example, the computer system may send an instruction to a cutting device, such as an edger or trimmer saw, to cause the cutting device to cut at least some of the wet wood from the rest of the workpiece. In other embodiments, the computer system may send an instruction to a labeling device (e.g., a printer, a projector, etc.) to cause the labeling device to print or project information about the wet spot onto the workpiece.

The workpiece may be processed as wet material or dry material based at least in part on the results of the wet spot detection. For example, a workpiece classified as wet material may be dried under different conditions, and/or with other workpieces classified as wet material.

Figure 17:
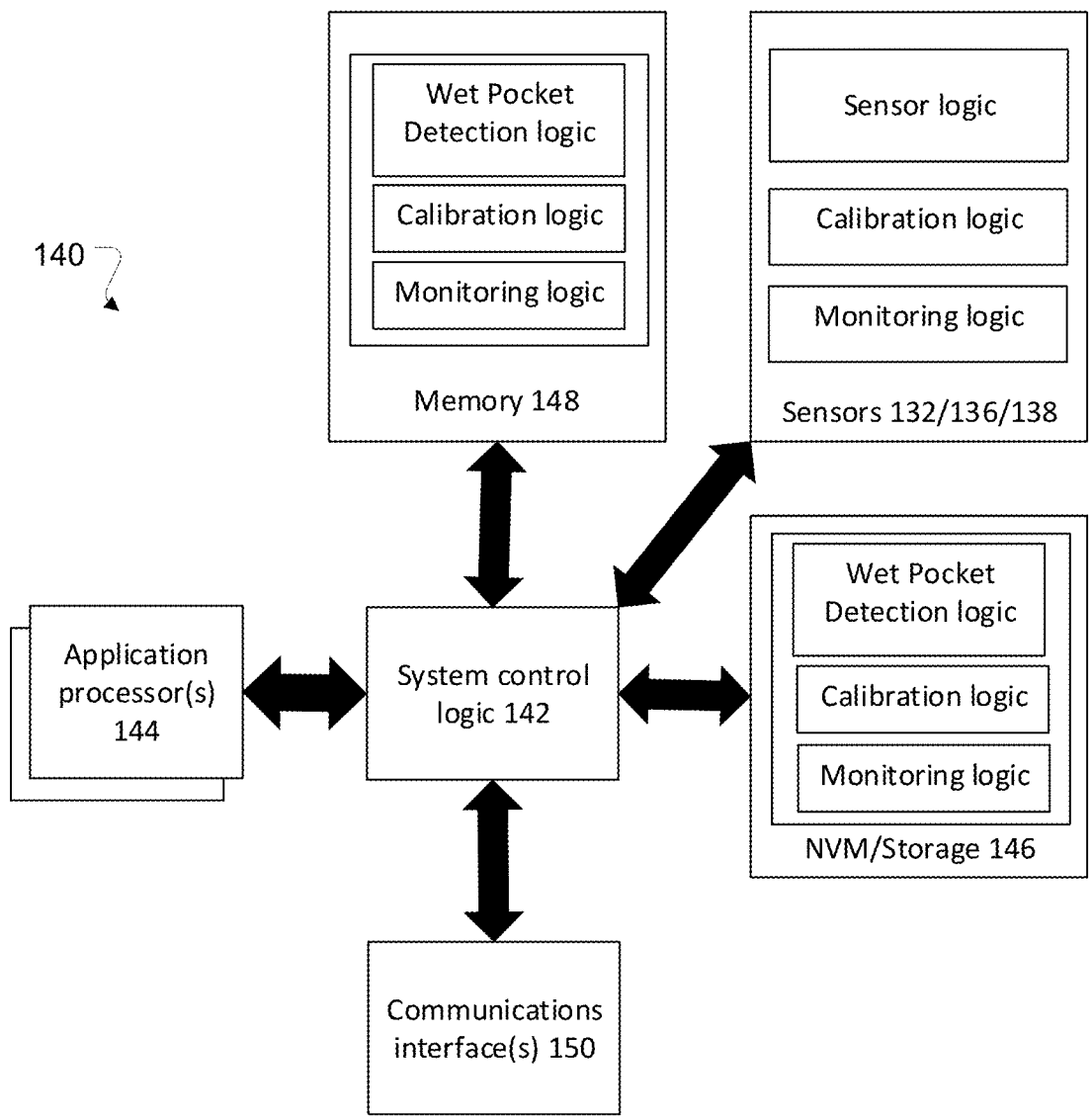
FIG. 17 is a schematic diagram of a computer system configured to perform wet spot detection methods as described herein, all in accordance with various embodiments.

FIG. 17 illustrates an example of a computer system 140 suitable for performing some or all of the operations/methods described herein, in accordance with various embodiments. Computer system 140 may have some or all of the features described herein with regard to various computer systems, and/or some or all of the functionality described herein with regard to scanners. For example, in some embodiments computer system 140 may be integrated with a scanner (e.g., scanner 130).

As illustrated, computer system 140 may include system control logic 142 coupled to at least one of the processor(s) 144, memory 148 coupled to system control logic 142, non-volatile memory (NVM)/storage 146 coupled to system control logic 142, and one or more communications interface(s) 150 coupled to system control logic 142. In various embodiments, system control logic 142 may be operatively coupled with one or more scanners (e.g., scanner 130), sensors (e.g., sensors 132, sensors 136/138) and/or an output device (e.g., a display, keyboard, mouse, touchscreen, etc.). In various embodiments the processor(s) 144 may be a processor core.

System control logic 142 may include any suitable interface controller(s) to provide for any suitable interface to at least one of the processor(s) 144 and/or any suitable device or component in communication with system control logic 142. System control logic 142 may also interoperate with the scanner(s)/sensor(s) and/or the output device(s). In various embodiments, the output device may include a display.

System control logic 142 may include one or more memory controller(s) to provide an interface to memory 148. Memory 148 may be used to load and store data and/or instructions, for example, for various operations of a wet spot detection method (e.g., wet pocket detection logic, calibration logic, and/or monitoring logic). In one embodiment, system memory 148 may include any suitable volatile memory, such as suitable dynamic random access memory ("DRAM"). In some embodiments, system control logic 142 may include one or more input/output ("I/O") controller(s) to provide an interface to NVM/storage 146 and communications interface(s) 150.

NVM/storage 146 may be used to store data and/or instructions. NVM/storage 146 may include any suitable non-volatile memory, such as flash memory, for example, and/or any suitable non-volatile storage device(s), such as one or more hard disk drive(s) ("HDD(s)"), one or more solid-state drive(s), one or more compact disc ("CD") drive(s), and/or one or more digital versatile disc ("DVD") drive(s), for example.

The NVM/storage 146 may include a storage resource that may physically be a part of a device on which computer system 140 is installed, or it may be accessible by, but not necessarily a part of, the device. For example, the NVM/storage 146 may be accessed over a network via the communications interface(s) 150.

System memory 148, NVM/storage 146, and/or system control logic 142 may include, in particular, temporal and persistent copies of wet pocket detection logic, calibration logic, and/or monitoring logic. The calibration logic, if present, may equalize the outputs from overlapping individual sensor units (i.e., of tracheid sensors) and/or correct image distortions caused by lens contaminations. The tracheid monitoring logic, if present, may identify and compensate for sensor lens contamination events. The wet pocket detection logic may use data collected by the tracheid sensors (and optionally color vision sensors and/or other sensors), and/or data generated by the calibration/tracheid monitoring logic, to detect wet spots on wood workpieces as described herein.

Communications interface(s) 150 may provide an interface for computer system 142 to communicate over one or more network(s) and/or with any other suitable device. Communications interface(s) 150 may include any suitable hardware and/or firmware, such as a network adapter, one or more antennas, a wireless interface, and so forth. In various embodiments, communication interface(s) 150 may include an interface for computer system 142 to use NFC, optical communications (e.g., barcodes), BlueTooth or other similar technologies to communicate directly (e.g., without an intermediary) with another device. In various embodiments, the wireless interface may interoperate with radio communications technologies such as, for example, WCDMA, GSM, LTE, and the like.

The capabilities and/or performance characteristics of processors 144, memory 148, and so forth may vary. In various embodiments, computer system 142 may include, but is not limited to, a smart phone, a computing tablet, a laptop computer, a desktop computer, and/or a server. In various embodiments computer system 142 may be, but is not limited to, one or more servers known in the art.

In one embodiment, at least one of the processor(s) 144 may be packaged together with system control logic 142 and/or wet pocket detection logic. For example, at least one of the processor(s) 144 may be packaged together with system control logic 142 and/or wet pocket detection logic to form a System in Package ("SiP"). In another embodiment, at least one of the processor(s) 144 may be integrated on the same die with system control logic 142 and/or positioning logic. For example, at least one of the processor(s) 144 may be integrated on the same die with system control logic 142 and/or positioning logic to form a System on Chip ("SoC").

The computer system 142 may be configured to perform any or all of the calculations, operations, and/or functions described above and/or in the Figures.

In various embodiments, the computer system may analyze the tracheid sensor image data and color image data to identify any defects along the imaged surface(s) of the workpiece. If the computer system has tracheid correction logic and/or tracheid monitoring logic as described above, the correction/monitoring logic may be used to adjust the tracheid sensor image data, and the computer system may use the adjusted data. Alternatively, the computer system may use unadjusted tracheid sensor image data, or tracheid sensor image data that has been adjusted by other means or processes.

The wet pocket detection logic may apply an adaptive threshold to the color image data. Each of the color channels (red, green, and blue) may be processed independently to create background images. The background images may be used as a basis for determining a threshold value. For example, the threshold value may represent an average intensity of clear (non-defective) wood. In some embodiments, the defect detection logic may determine a local average intensity value for the workpiece by excluding any extreme (low or high) intensity values. The local average intensity value may be scaled and applied to the color channels (e.g., to each of the three background images). Pixels that exceed the local average intensity value may be thresholded, and the resulting binary images may be used in additional processing operations.

The wet pocket detection logic may apply a fixed threshold to each of the two tracheid channels (i.e., to the laser spot area channel and the laser spot aspect ratio channel). For example, the wet pocket detection logic may generate a laser spot aspect ratio image and a laser spot area image by assigning intensity values to the pixels in those images based on the aspect ratio and area values of the corresponding laser spots. Pixels with intensity values that exceed the individual channel threshold may be segmented. The resulting thresholded images may be dilated to fill in gaps and enlarge the objects/regions of interest.

The wet pocket detection logic may combine the resulting images (the color channel images and the segmented tracheid channel images) with AND operation.

Exclusions may be applied for knots, wane, board (or flitch) edges, and/or other features, and the exclusions (if any) may be combined with previously combined individual channels. Dilation/erosion operations may be applied, and the resulting binary image may be segmented to define connected regions. The connected regions may be examined for size, and regions that are too small or too large regions may be rejected. The remaining regions may be applied to final grade determining logic, which combines detected wet spots from different surfaces of the workpiece (e.g., top and bottom). All wet spots may be summed to determine whether the workpiece (or a portion thereof) should be classified as wet spec material.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A non-transitory computer-readable medium comprising instructions operable, upon execution by a processor of a computer, to cause the computer to:
   receive first image data representing one or more first images of laser spots on at least one surface of a wood workpiece traveling along a path of flow;
   process the first image data to determine aspect ratio values and area values for at least some of the laser spots;
   identify one or more wet spots on the surface of the wood workpiece based at least in part on the aspect ratio values and the area values of the respective laser spots; and
   in response to identifying the one or more wet spots, send an instruction to a machine center to thereby divert the wood workpiece from the path of flow, or to sort or cut the wood workpiece, or to designate the wood workpiece as wet material, or
   cause a display to display a representation of the surface of the wood workpiece and the one or more wet spots on the surface of the wood workpiece.

2. The computer-readable medium of claim 1, wherein the instructions are operable, upon execution by the processor, to cause the computer to:
   compare the determined aspect ratio values to an aspect ratio threshold value,
   compare the determined area values to an area threshold value,
   determine, based on the comparison, that the aspect ratio values of one or more groups of the laser spots are less than the aspect ratio threshold value and that the area values of the one or more groups of the laser spots exceeds the area threshold value, and
   identify a corresponding one or more areas of the surface of the wood workpiece as the one or more wet spots.

3. The computer-readable medium of claim 2, wherein the instructions are further operable, upon execution by the processor, to cause the computer to:
   process the first image data to determine angles for at least some of the laser spots;
   compare the angles to a range of expected angles; and
   identify or confirm the one or more wet spots based at least in part on the comparison of the angles to the range of expected angles.

4. The computer-readable medium of claim 3, wherein the range of expected angles is a range of expected angles for a laser spot on clear dry wood, and wherein the instructions are operable, upon execution by the processor, to cause the computer to:
   identify or confirm the one or more wet spots based at least in part on a determination that the angles of at least some of the one or more groups of wet spots are outside of the range of expected angles.

5. The computer-readable medium of claim 2, wherein the instructions are further operable, upon execution by the processor, to cause the computer to:
   identify a first portion of the surface as a potential non-moisture defect based at least on a determination that the aspect ratio values of the laser spots on said first portion are less than the aspect ratio threshold value and the area values of the laser spots on said first portion do not exceed the area threshold value.

6. The computer-readable medium of claim 1, wherein the first image data is collected by one or more linear sensors with photosensitive elements, the photosensitive elements correspond to rows of the one or more first images, and the instructions are operable, upon execution by the processor, to:
   generate an area image based on the area values, wherein generating the area image includes converting the area values to respective first pixel intensity values;
   generate an aspect ratio image based on the aspect ratio values, wherein generating the aspect ratio image includes converting the aspect ratio values to respective second pixel intensity values;
   determine correction coefficients for at least some of the photosensitive elements based on intensity values for said photosensitive elements and a target intensity value; apply the correction coefficients to the respective pixel intensity values of the area image and the aspect ratio image to thereby adjust the pixel intensity values of the images; and identify the one or more wet spots on the surface of the wood workpiece based at least in part on the adjusted pixel intensity values of the one or more first images.

7. The computer-readable medium of claim 1, wherein the first image data is collected by a sensor with photosensitive elements, and the instructions are operable, upon execution by the processor, to cause the computer to:
receive second image data collected by the sensor, wherein the second image data represent additional images of additional laser spots on one or more surfaces of a plurality of additional wood workpieces traveling along the path of flow, and the photosensitive elements correspond to rows of the first and second images;
analyze the first and second images to determine, for at least some of said wood workpieces, a percentage of pixels that are outside of an expected range of intensity values for defect-free wood;
compare the determined percentages for a predetermined number of the wood workpieces to an expected out-of-range percentage; and
in response to a determination that said determined percentages exceed the expected out-of-range percentage, cause an output device to output an indication that the sensor, or one or more of the photosensitive elements, is contaminated.

8. The computer-readable medium of claim 1, wherein the instructions are further operable, upon execution by the processor, to cause the computer to:
receive second image data representing one or more second images of said surface of the wood workpiece traveling along the path of flow, the one or more second images being color images;
process the second image data to determine color values for a plurality of portions of the surface of the wood workpiece; and
identify or confirm the one or more wet spots on the surface of the wood workpiece based at least in part on the color values.

9. The computer-readable medium of claim 8 wherein the instructions are operable, upon execution by the processor, to cause the computer to:
compare the determined color values to a threshold color value, wherein the threshold color value represents a color of clear dry wood, and
identify or confirm the one or more wet spots on the surface of the wood workpiece based at least in part on a determination that the color of a corresponding one or more of said portions of the wood workpiece is darker than the color of clear dry wood.

10. The computer-readable medium of claim 8, wherein the instructions are operable, upon execution by the processor, to cause the computer to:
generate an area image based on the area values;
generate an aspect ratio image based on the aspect ratio values;
generate a plurality of color channel images based on the second image data;
adjust one or both of the area image and the aspect ratio image based at least on prior image data or a range of expected intensity values;
process the adjusted area image, the adjusted aspect ratio image, and the color channel images;
combine the processed images into a combined image;
process the combined image; and
identify the one or more wet spots based at least on the combined image.

11. The computer-readable medium of claim 1, wherein the first image data is collected by one or more linear sensors with photosensitive elements, the photosensitive elements correspond to rows of the one or more first images, and the instructions are operable, upon execution by the processor, to cause the computer to identify the one or more wet spots by:
converting the aspect ratio values to respective first pixel values to generate an aspect ratio image,
converting the area values to respective second pixel values to generate an area image,
adjusting the aspect ratio image and the area image based at least on prior image data collected by the one or more sensors,
processing the aspect ratio image and the area image to obtain binary images,
combining the binary images to obtain a combined image, and
processing the combined image to identify one or more regions of interest, wherein the one or more regions of interest corresponds to the one or more wet spots.

12. A wet pocket detection system comprising:
a tracheid sensor having at least one laser light source and at least one camera; and
a computer system operatively coupled with the tracheid sensor, wherein the computer system is programmed with non-transitory instructions operable, upon execution by a processor of the computer system, to cause the computer system to:
receive from the tracheid sensor one or more images of laser spots on at least one surface of a wood workpiece traveling along a path of flow;
process the one or more images to determine aspect ratio values and area values for at least some of the laser spots;
identify one or more wet spots on the surface of the wood workpiece based at least in part on the aspect ratio values and the area values; and
in response to identifying the one or more wet spots, send an instruction to a machine center to thereby cause the machine center to divert the wood workpiece from the path of flow, to cut the wood workpiece, to sort the wood workpiece, or to designate the wood workpiece as wet material or dry material, or
cause a display to display a representation of the surface of the wood workpiece and the one or more wet spots.

13. The wet pocket detection system of claim 12, wherein the tracheid sensor is a dot vector laser tracheid imaging sensor, the at least one laser light source is a plurality of laser light sources arranged to project a row of the laser spots, and the at least one camera is includes one or more line cameras.

14. The wet pocket detection system of claim 12, further including one or more color vision sensors arranged to capture images of said one or more surfaces of the wood workpiece, wherein the instructions are operable, upon execution by the processor, to cause the computer system to identify the one or more wet spots on the one or more surfaces of the wood workpiece based at least in part on color image data received from the one or more color vision sensors.

15. The wet pocket detection system of claim 14, wherein the instructions are operable, upon execution by the processor, to cause the computer system to identify the one or more wet spots by:

converting the aspect ratio values to respective first pixel values to generate an aspect ratio image, converting the area values to respective second pixel values to generate an area image, adjusting the aspect ratio image and the area image based at least on prior image data collected by the one or more sensors, processing the color image data to obtain color channel images, processing the aspect ratio image, the area image, and the color channel images to obtain respective binary images, combining the binary images to obtain a combined image, and processing the combined image to identify one or more regions of interest, wherein the one or more regions of interest corresponds to the one or more wet spots.

16. A method of processing wood workpieces, the method comprising:
   determining an aspect ratio value and an area value of each of a plurality of laser spots based on one or more images of the laser spots on one or more surfaces of a wood workpiece;
   identifying one or more wet spots on the one or more surfaces of the wood workpiece based at least on the aspect ratio values and the area values;
   classifying the wood workpiece as wet material or dry material based at least on the one or more wet spots; and
   selecting a drying schedule for the wood workpiece based at least on the classification, or sending an instruction to a machine center to divert, sort, cut, or label the wood workpiece based at least on the classification, or causing a display to display a representation of the one or more surfaces of the wood workpiece and the one or more wet spots.

17. The method of claim 16, wherein identifying the one or more wet spots includes:
   converting the aspect ratio values to respective first pixel values to generate an aspect ratio image,
   converting the area values to respective second pixel values to generate an area image,
   processing the aspect ratio image and the area image to obtain binary images,
   combining the binary images to obtain a combined image, and
   processing the combined image to identify one or more regions of interest, wherein the one or more regions of interest corresponds to the one or more wet spots.

18. The method of claim 17, wherein classifying the wood workpiece as wet material or dry material includes:
   summing the wet spots identified on the one or more surfaces of the wood workpiece to determine a sum value,
   determining a wet spot value based at least on the sum value,
   comparing the wet spot value to a classification threshold value, and
   classifying the wood workpiece as wet material or dry material based on the comparison.

19. The method of claim 16, wherein identifying the one or more wet spots includes:
   obtaining one or more second images of the one or more surfaces, wherein the second images are captured by one or more color vision cameras,
   processing the color image data to generate color channel images,
   converting the aspect ratio values to respective first pixel values to generate an aspect ratio image,
   converting the area values to respective second pixel values to generate an area image,
   processing the aspect ratio image, the area image, and the color channel images to obtain respective binary images,
   combining the binary images to obtain a combined image, and
   processing the combined image to identify one or more regions of interest, wherein the one or more regions of interest corresponds to the one or more wet spots.

20. The method of claim 19, further including identifying an additional one or more wet spots on one or more additional surfaces of the wood workpiece, wherein classifying the wood workpiece as wet material or dry material includes:
   summing the wet spots identified on the one or more surfaces of the wood workpiece to determine a sum value,
   determining a wet spot value based at least on the sum value,
   comparing the wet spot value to a classification threshold value, and
   classifying the wood workpiece as wet material or dry material based on the comparison.

* * * * *